(12) United States Patent
Hodgson et al.

(10) Patent No.: US 10,888,572 B2
(45) Date of Patent: Jan. 12, 2021

(54) DIETARY AND NUTRITIONAL COMPOSITIONS AND METHODS OF USE

(71) Applicant: Brightside Innovations, Inc., La Habra, CA (US)

(72) Inventors: Donald F. Hodgson, Fullerton, CA (US); Crispin G. S. Eley, Fullerton, CA (US)

(73) Assignee: BIO-UP MIMETIC TECHNOLOGIES, INC., La Habra, CA (US)

( * ) Notice: Subject to any disclaimer, the term of this patent is extended or adjusted under 35 U.S.C. 154(b) by 0 days.

(21) Appl. No.: 15/368,484

(22) Filed: Dec. 2, 2016

(65) Prior Publication Data

US 2017/0080000 A1    Mar. 23, 2017

Related U.S. Application Data

(63) Continuation of application No. 14/379,226, filed as application No. PCT/US2013/026548 on Feb. 16, 2013, now abandoned.

(60) Provisional application No. 61/599,786, filed on Feb. 16, 2012.

(51) Int. Cl.
| | |
|---|---|
| *A61K 31/685* | (2006.01) |
| *A23L 33/00* | (2016.01) |
| *A23L 33/12* | (2016.01) |
| *A61K 9/127* | (2006.01) |
| *A61K 47/14* | (2017.01) |
| *A61K 9/00* | (2006.01) |
| *A23L 33/11* | (2016.01) |
| *A61K 31/202* | (2006.01) |
| *A61K 31/231* | (2006.01) |
| *A61K 31/56* | (2006.01) |
| *A61K 9/10* | (2006.01) |
| *A61K 31/23* | (2006.01) |
| *A61K 36/31* | (2006.01) |
| *A61K 36/53* | (2006.01) |
| *A61K 36/899* | (2006.01) |

(52) U.S. Cl.
CPC ............ *A61K 31/685* (2013.01); *A23L 33/11* (2016.08); *A23L 33/12* (2016.08); *A23L 33/30* (2016.08); *A61K 9/0095* (2013.01); *A61K 9/10* (2013.01); *A61K 9/127* (2013.01); *A61K 31/202* (2013.01); *A61K 31/23* (2013.01); *A61K 31/231* (2013.01); *A61K 31/56* (2013.01); *A61K 36/31* (2013.01); *A61K 36/53* (2013.01); *A61K 36/899* (2013.01); *A61K 47/14* (2013.01); *A23V 2002/00* (2013.01)

(58) Field of Classification Search
CPC ............................. A61K 9/127; A61K 31/685
See application file for complete search history.

(56) References Cited

U.S. PATENT DOCUMENTS

| | | | |
|---|---|---|---|
| 4,174,296 A | 11/1979 | Kass | |
| 4,235,793 A | 11/1980 | Betzing | |
| 5,853,755 A * | 12/1998 | Foldvari | ............... A61K 9/0014 424/450 |
| 6,177,103 B1 | 1/2001 | Pace et al. | |
| 7,465,717 B2 | 12/2008 | Dexter et al. | |
| 9,353,137 B2 * | 5/2016 | Amoabediny | ........... C07F 9/103 |
| 2005/0058700 A1 | 3/2005 | Wachter et al. | |
| 2006/0193905 A1 | 8/2006 | Ehringer et al. | |
| 2011/0212167 A1 * | 9/2011 | Ali | ........................ A61K 9/0014 424/450 |
| 2011/0318406 A1 * | 12/2011 | Eley | ...................... A23L 33/115 424/450 |

FOREIGN PATENT DOCUMENTS

| | | |
|---|---|---|
| GB | 1113241 | 5/1968 |
| GB | 2 050 287 A | 1/1981 |
| JP | 55-153713 A | 11/1980 |
| JP | 7-48247 A | 2/1995 |
| JP | 8-151334 | 6/1996 |
| JP | 2004-359647 A | 12/2004 |
| JP | 2004-359648 A | 12/2004 |
| KR | 2003-0084120 | 11/2003 |
| KR | 2011-0076068 | 7/2011 |
| WO | WO 2011/018480 A1 | 2/2011 |
| WO | WO 2011/162818 A2 | 12/2011 |

OTHER PUBLICATIONS

Scholfield, Composition of Soybean Lecithin, JAOCS (1981), pp. 889-892.*
JN Israelachvili, S Marcelja, RG Horn. "Physical principles of membrane organization." Quarterly Reviews of Biophysics, vol. 13 Issue 2 (1980), pp. 121-200. (Year: 1980).*
Rainer H. Mueller, Karsten Maeder, Sven Gohla. "Solid lipid nanoparticles (SLN) for controlled drug delivery—a review of the state of the art." European Journal of Pharmaceutics and Biopharmaceutics, vol. 50 (2000) 161-177 (Year: 2000).*
KH Ramteke, SA Joshi, SN Dhole. "Solid Lipid Nanoparticle: A Review." IOSR Journal of Pharmacy, vol. 2 Issue, Nov.-Dec. 2012, pp. 34-44. (Year: 2012).*
Office action dated Nov. 1, 2016 in corresponding JP Patent Application No. 2014-557857, including Eng. translation 8pp.
Office action dated Nov. 17, 2016 in corresponding CN Patent Application No. 201380020372.4, including Eng. translation 16pp.
Office action dated Dec. 29, 2015 in corresponding Chinese application No. 201380020372.4 including English translation, 15pp.

(Continued)

*Primary Examiner* — Isaac Shomer
(74) *Attorney, Agent, or Firm* — Lewis Roca Rothgerber Christie LLP

(57) ABSTRACT

A hydrated lecithin carrier vesicle composition includes lecithin and a triglyceride source or fatty acid in conditioned water. The disclosed compositions may be used for controlling appetite, weight loss, modulating effects from alcohol consumption, and/or delivering active agents to the small intestine.

21 Claims, 10 Drawing Sheets

(56) References Cited

OTHER PUBLICATIONS

International Search Report and Written Opinion for International Application No. PCT/US2013/026548, dated Jun. 2, 2013, 13pp.
Adams et al., "Natural Appetite Suppressants for Safe, Effective Weight Loss", Truth Publishing.com (2009), pp. 1-113.
Zambiazi et al., "Fatty Acid Composition of Vegetable Oils and Fats", B.CEPPA, Curitiba (2007), vol. 25, No. 1, pp. 111-120.
Yingzi Wu, et al., "Fractionation of Crude Soybean Lecithin with Aqueous Ethanol," *Journal of the American oil Chemists' Society*, 2004, 81: 697-704.
Cargill, "Lecithin manufacturing process," 2014, pp. 1-4.
Lecithin, prepared at the 41st JECFA (1993), published in FNP 52 Add 2 (1993) superseding specifications prepared at the 30th JECFA (1986), published in FNP 37 (1986) and FNP 52 (1992). Metals and arsenic specifications revised at the 61st JECFA (2003). An ADI not limited' was established at the 17th JECFA (1973), 4 pages.
Schulze, V.E., et al., Contributions to Knowledge of Plant Extractable Lecithins, Partial English Translation, 1904, 28 (2) 3 pages.
Wu, Y., et al. Soybean Lecithin Fractionation and Functionality, Journal of the American Oil Chemists Society, 2003, vol. 80, No. 4, pp. 319-326.
Wu, Y., et al., Phospholipid Class and FA Compositions of Modified Soybeans Processed with Two Extraction Methods, Journal of the American Oil Chemists Society, 2003, vol. 80, No. 2, pp. 127-132.
Zuidam, N.J. et al., Encapsulation Technologies for Active Food Ingredients and Food Processing, Springer Nature Pub., 2 excerpts from Chapter 2.2 p. 21 and Chapter 8.2, 2009, 1 page, ISBN 978-1-4419-1008-0.
Vandamme, T. and Anton, N., "Low-energy nanoemulsification to design veterinary controlled drug delivery devices", International Journal of Nanomedicine, 2010:5, pp. 867-873.
Nakonechny, F. et al, "Olive Oil-Based Delivery of Photosensitizers for Bacterial Eradication", Olive Oil—Constituents, Quality, Health Properties and Bioconversions, Chapter 25, pp. 472-492, downloaded from www.intechopen.com/books/olived-oil-constituents-quality-health-properties-and-bioconversions/olive-oil-based-delivery-of-photosensitizers-for-bacterial-eradication (2012).
Kucerka, N. et al., "Fluid phase lipid areas and bilayer thicknesses of commonly used phosphatidylcholines as a function of temperature", Biochimica et Biophysica Acta, 1808 (2011) pp. 2761-2771.
Nagle, F, and Wilkinson, D.A., "Lecithin Bilayers Density Measurements and Molledular Interactions", Biophys. J., 006-3495/78/0801, pp. 159-175, 1977.
Lasch, J. et al., "Liposomes, Second Edition, A Practical Approach," Section 3.1, Chapter 1 titled "Preparation of Liposomes," Torchillin and Weissig eds., *Oxford University Press*, 2003 ISBN 0 19 963655 9, one sheet.
Hughes, L. et al., "Choose Your Label Wisely: Water-Soluble Fluorophores Often Interact with Lipid Bilayers", Plos One, 2014, vol. 9, Issue 2, e87679, 8 pages, downloaded from https://doi.org/10.1371/journal.pone.0087649.

\* cited by examiner

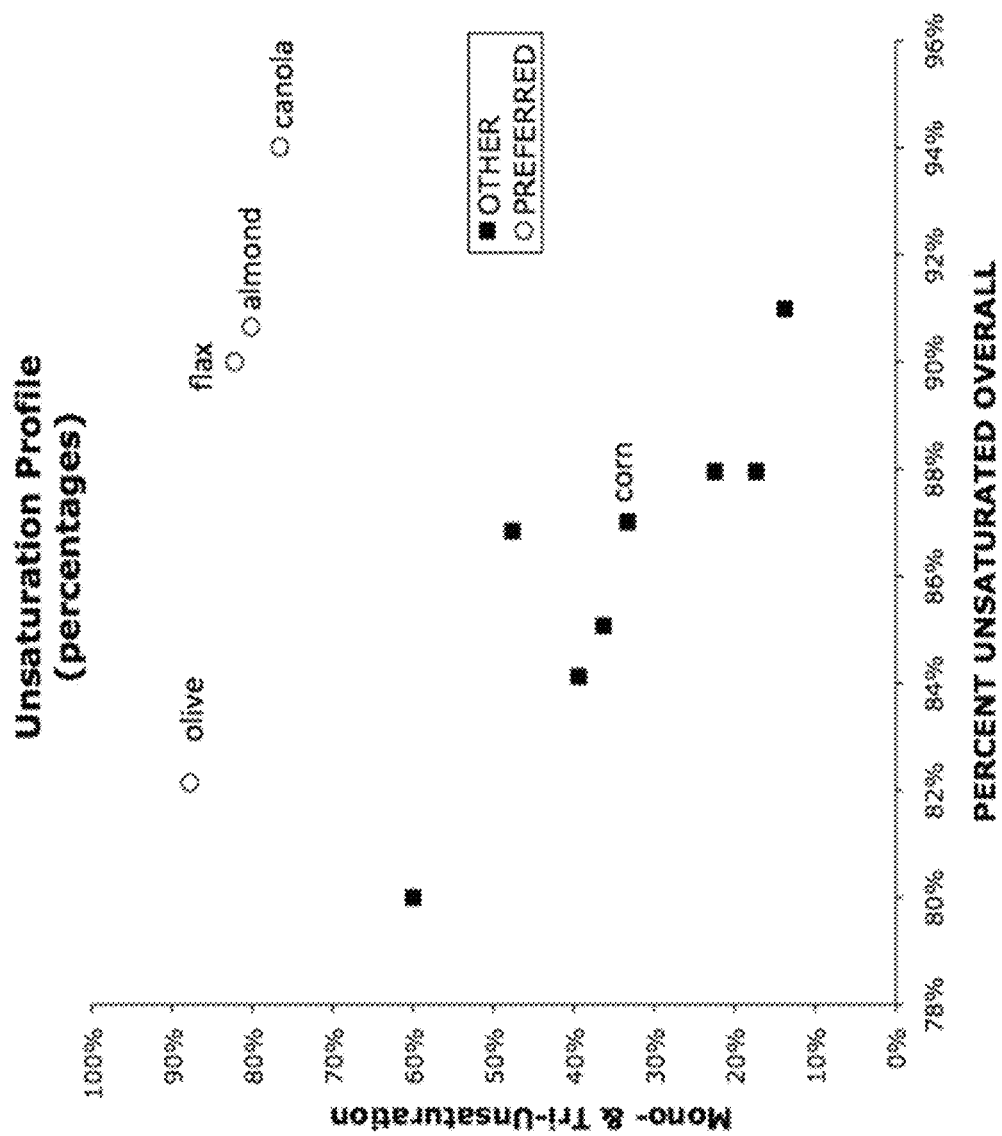

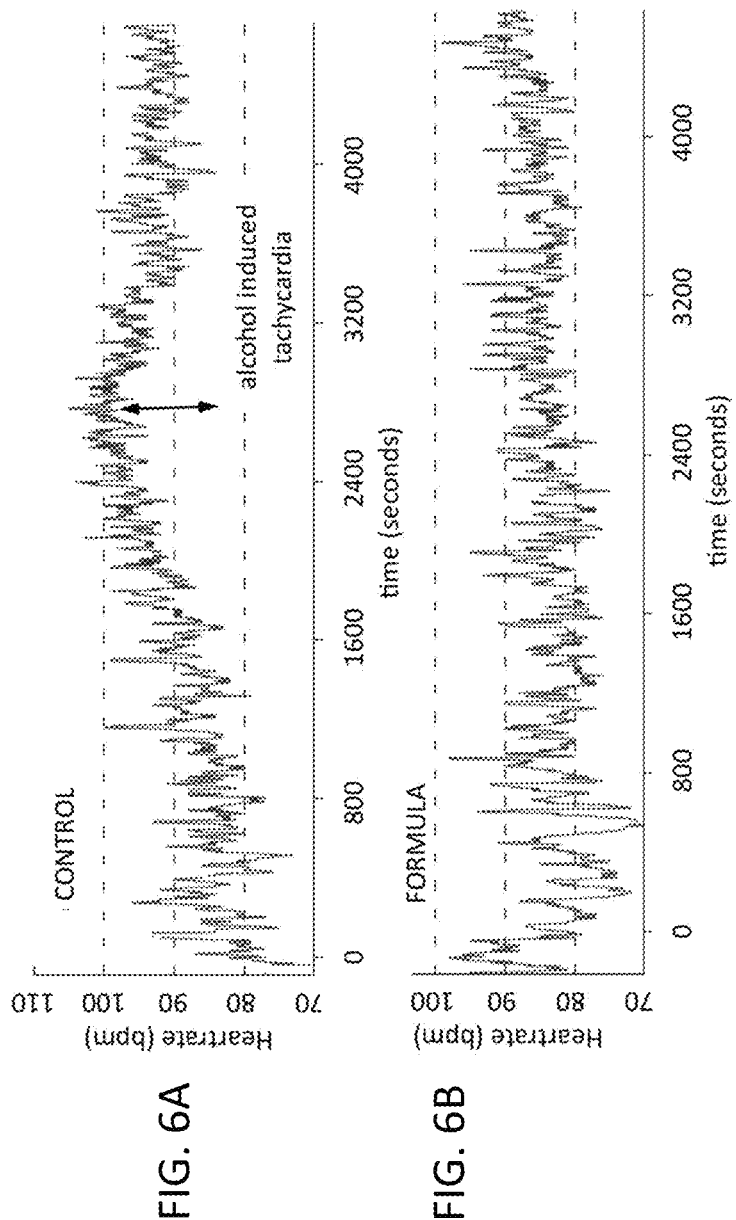

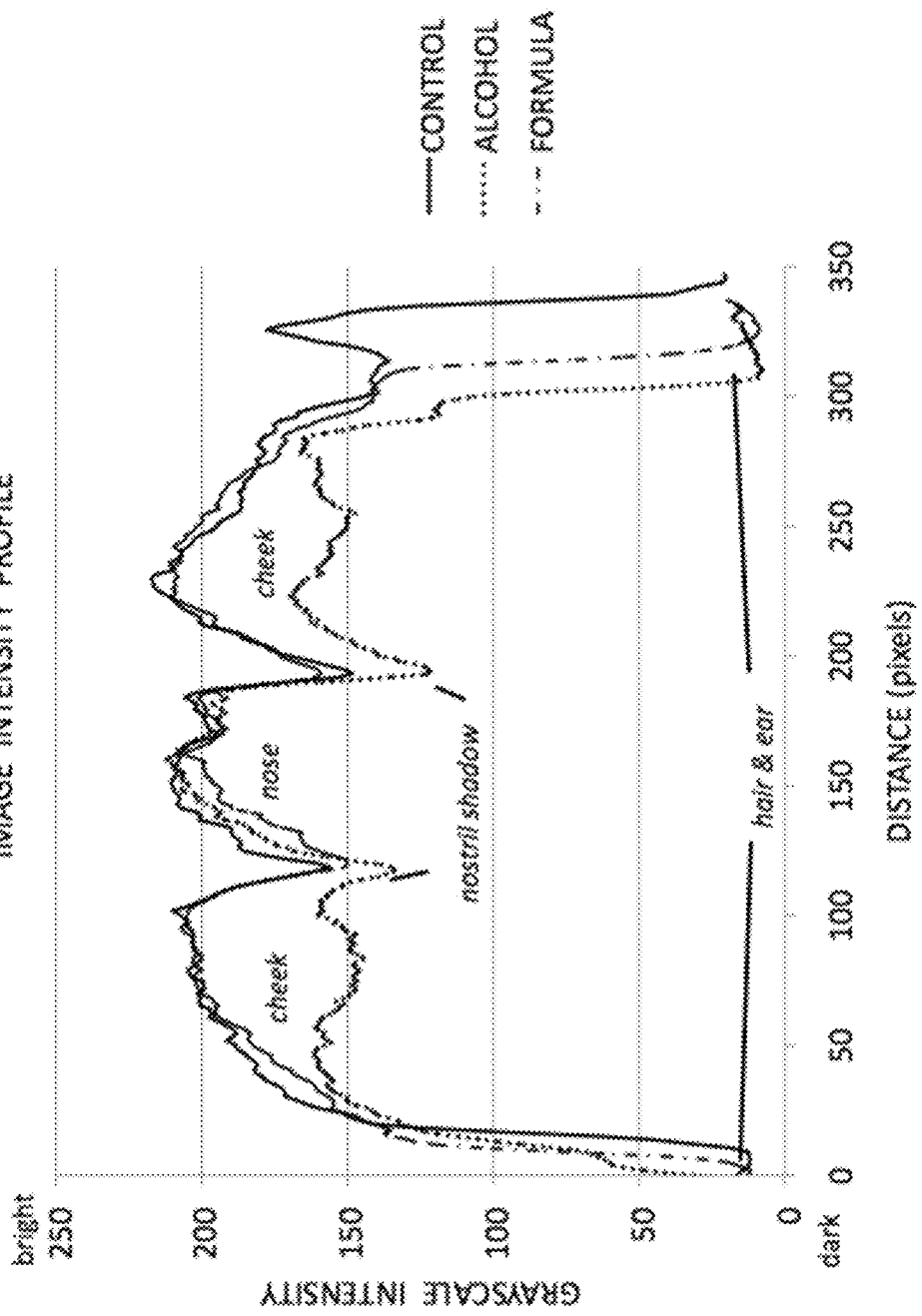

DIETARY AND NUTRITIONAL COMPOSITIONS AND METHODS OF USE

CROSS-REFERENCE TO RELATED APPLICATION(S)

The present application is a continuation of and claims priority to and the benefit of U.S. application Ser. No. 14/379,226 filed Aug. 15, 2014 which is a national phase patent application of International Application No. PCT/US2013/026548 filed Feb. 16, 2013 which claims priority to and the benefit of U.S. Provisional Application Ser. No. 61/599,786 filed on Feb. 16, 2012, the entire contents of which are incorporated herein by reference.

FIELD

Embodiments of the present invention are directed to lecithin and triglyceride or fatty acid carrier compositions and use of these compositions for improved health.

BACKGROUND

Metabolic syndrome refers to a group of risk factors that raises the risk of heart disease and other health problems, such as diabetes and stroke. The risk factors include high blood pressure, obesity, high cholesterol, and insulin resistance. In particular, a person's risk of having metabolic syndrome is closely linked to the person being overweight or obese and/or lacking of exercise. Obesity is thus related to the increased prevalence of diabetes, cancer, hypertension, high cholesterol, and coronary artery disease. In addition, co-morbidities involving the central nervous, such as depression, anxiety, substance abuse, insomnia and chronic pain may be complicated by obesity.

For both health and body image reasons, there are many individuals who wish to lose weight and/or desire to retain a lower weight after having lost weight. In the majority of cases, weight control is simply dependent on the balance between caloric intake (food/beverage) and caloric output (exercise). A widely pursued goal is the facile reduction of caloric intake.

SUMMARY

In some embodiments of the present invention, a composition includes a stable homogenous dispersion of a vesicle and conditioned water, has a membrane and an aqueous phase, and includes lecithin, and a triglyceride source and/or at least one fatty acid dispersed therein.

In some embodiments of the present invention, methods for decreasing appetite in a human or animal includes includes administering the composition to the human or animal. In some embodiments, methods for aiding weight loss in a human or animal includes administering the composition to the human or animal.

In some embodiments of the present invention, methods for increasing delivery of an agent to the body including the circulatory system and bloodstream of a human or animal include administering the composition to the human or animal.

In some embodiments of the present invention, methods of attenuating facial flushing and increases in heart rate of a human or animal caused by consumption of alcohol, include administering the composition to the human or animal.

BRIEF DESCRIPTION OF THE DRAWINGS

These and other features and advantages of the present invention will be better understood by reference to the following detailed description when considered in conjunction with the accompanying drawings, in which:

FIG. 4A is a graph of the percent of mono- and tri-unsaturation versus the overall percent of unsaturation for the indicated triglyceride sources, as described in Example 5, according to some embodiments of the present invention.

FIG. 6A is a heart rate trace taken on an individual after consumption of alcohol without prior consumption of a disclosed composition, as described in Example 7;

FIG. 6B is a heart rate trace taken on the same individual as in FIG. 6A after consumption of alcohol with prior consumption of the disclosed composition, as described in Example 7, according to embodiments of the present invention.

FIG. 7B is an image intensity profile of the analyzed photo images taken along the image line depicted in FIG. 7A of the face of the individual tested in FIGS. 6A and 6B, as described in Example 7, according to embodiments of the present invention.

DETAILED DESCRIPTION

Figure 1:
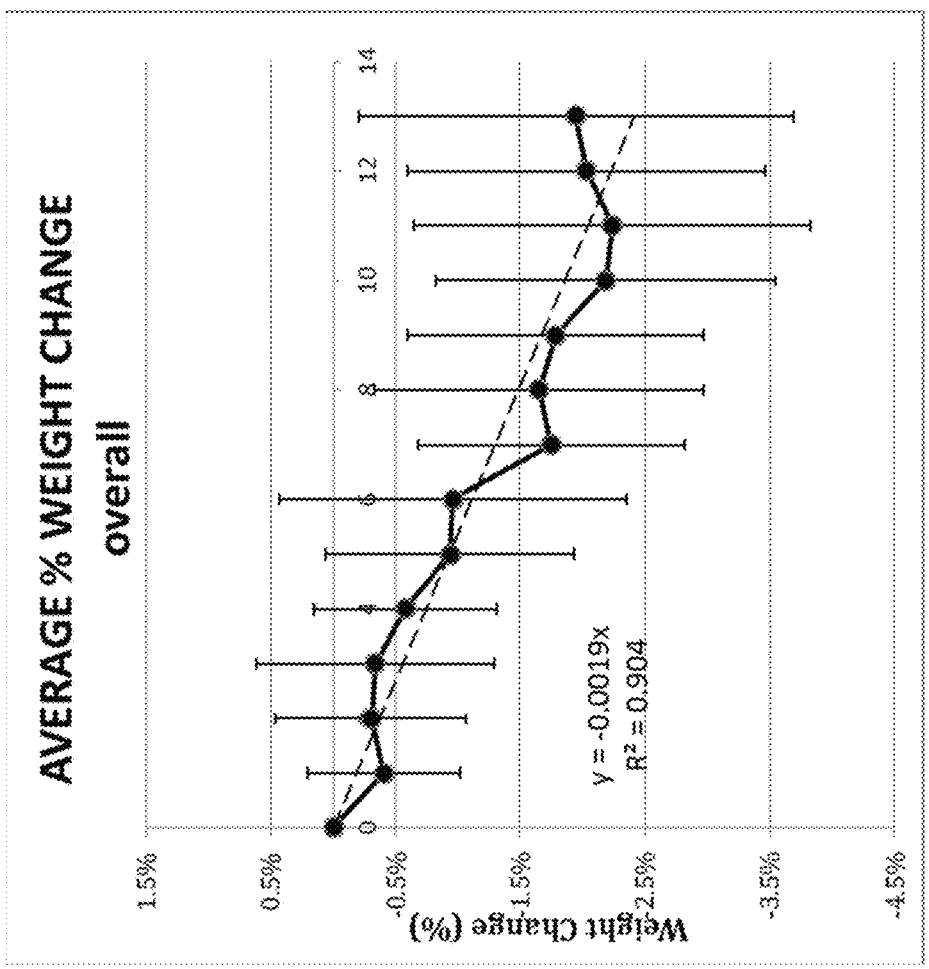
FIG. 1 is a graph showing the average percent of weight change amongst all 12 volunteers for each of 14 days as indicated and described in Examples 1 and 2, according to some embodiments of the present invention.

According to embodiments of the present invention, a composition includes a mixture of triglyceride and lecithin dispersed in an aqueous medium. In some embodiments, the lecithin includes a hydrated lecithin carrier vesicle. As used herein, the terms "triglyceride/lecithin composition" and "triglyceride-lecithin mixture" are used interchangeably and refer to a hydrated lecithin carrier vesicle including triglyceride and/or triglyceride hydrolysis products, and conditioned water, or the homogeneous mixture of lecithin and triglyceride before hydration with conditioned water.

In some embodiments of the present invention, controlling appetite of a human or animal includes administering a triglyceride/lecithin composition to the human or animal. The method of decreasing appetite facilitate weight loss by reducing the quantities of food the person or animal consumes at normal meals, and reducing snacking between meals. For certain users, the compositions according to embodiments of the invention, may provide additional benefits, including improved self-image, and may increase the user's tolerance for alcohol or improve the user's nutrition. As used herein, "user" refers to a person or animal to which the disclosed composition is administered, by which the method of weight loss or weight control or alcohol tolerance is performed.

Embodiments of the invention relate to intermediate compositions and final compositions for administration to a user, and to applications of the compositions. The particular compositions include homogeneous mixtures of lecithin and dietary lipids, for example, triglycerides and their hydrolysis products, which may be prepared according to the methods described in U.S. patent application Ser. No. 13/135,057, titled Lecithin Carrier Vesicles and Methods of Making the Same, filed Jun. 23, 2011, the entire content of which is incorporated herein by reference. These compositions produce surprising effects on satiety, and thereby facilitate weight loss or weight control. These compositions also have the potential to moderate the rate and/or extent of uptake of other co-formulated, co-ingested or subsequently ingested food and beverage components. The particular triglyceride mixtures of certain embodiments include a low intake of fat (approximately 2.5-5.0 grams, i.e., ½-1 teaspoon) consumed prior to meals. This has surprisingly been found to produce a sensation of satiety, and apparent moderation of caloric intake, that leads to weight loss. The onset of the effect is relatively rapid (e.g., within 20 minutes of consumption of the composition), and lasts several hours, based on reported observations. Without being bound to a particular explanation of the phenomenon, it is plausible that pre-emulsifying a relatively small amount of triglyceride with lecithin as disclosed herein, promotes rapid and efficient uptake of fat in the small intestine which in turn leads to sensations of having consumed a large amount of fat and hence a feeling of fullness. Although the present disclosure may refer to certain compositions being "ingested", it is understood that the compositions may also be "administered" in certain embodiments. As used herein, the term "ingested" refers to consumption of a composition by a human or animal. As used herein, the term "administered" refers to providing a composition to a human or animal for consumption.

In some embodiments, in addition to the concentrated dispersion of the lecithin-triglyceride mixture, consuming a volume of liquid that engenders a feeling of fullness provides for additional caloric intake control. A suitable volume is about 8 oz. or about 250 ml, but smaller or larger volumes can be used depending on the specific effect desired. For example, the concentrated dispersion can be diluted to the desired total volume.

In other embodiments, a triglyceride/lecithin composition may help in the metabolism of alcohol by slowing or delaying its uptake into the bloodstream. This mechanism allows for decreased blood alcohol content (BAC) and presumably lower blood levels of acetaldehyde, the initial alcohol breakdown product, leading in some cases to an increased tolerance for alcohol. An increased tolerance for alcohol may be most notably useful for users having low levels of aldehyde dehydrogenase in which ordinarily causes users to experience facial flushing and increased heart rate upon consumption of alcohol.

In other embodiments, a triglyceride/lecithin composition may include additional fatty acids. The "essential fatty acids" alpha-linoleic acid and linoleic acid are desired as they are required for biological processes, yet they are not synthesized by human, and, therefore must be consumed. These essential fatty acids are required for the biological synthesis of the omega-3 fatty acids, eicosapentaenoic acid (EPA) and docosahexaenoic acid (DHA), which are necessary for many basic cellular functions, thereby providing multiple health benefits to the user. As would be recognized by those of ordinary skill in the art, the term "essential fatty acids" is a term of art used to identify certain fatty acids, and does not indicate that the listed materials are essential or critical to the practiced embodiments of the present invention. In some embodiments, the triglyceride-lecithin composition includes at least one fatty acid. In some embodiments, a user's consumption of a triglyceride-lecithin composition including at least one fatty acid results in an increase in the amount of fatty acids found in the blood plasma of the user.

In some embodiments, the presently disclosed compositions may also include food-grade buffer ions, for example, citric acid (which is also a flavor agent) or phosphoric acid. There are many food acids, known as acidulants, that are commonly used in beverages and that are suitable for use in the present compositions. Non-limiting examples of acidulants include citric acid, phosphoric acid, acetic acid, lactic acid, malic acid, tartaric acid, and combinations thereof. In some situations, the content of lyotropic buffer ions of the acidulant may be limited when other formulation constraints (e.g., taste and buffer capacity at a particular pH) allow for decreasing or removing lyotropic buffer ions. In some embodiments, a triglyceride/lecithin composition includes citric acid for purposes of buffering the composition from the low pH of a user's stomach.

Common buffer systems include acceptable food acidulants and their salts—including both potassium and sodium. In some situations, potassium is used rather than sodium cations to keep the sodium content low, and the content of lyotropic ions minimized. For example, for citrate, tartrate or other polycarboxylic acid buffer anions, having an exemplary maximum concentration is 25 mM (expressed as the combined concentration of the corresponding acid and the anion). In another exemplary embodiment, the concentration of the acid and anion is less than 10 mM. In yet another embodiment, the concentration of the acid and anion is less than 2.5 mM. In still another embodiment, the polyvalent anionic buffer species are substantially absent. As used herein, the term "substantially" is used as a term of approximation and not a term of degree, and is intended to account for inherent deviations in a listed value caused by the normal uncertainty involved in measurements and calculations. In some embodiments, the ratio of buffer to lecithin is not less than about 0.1:1 (mole:mole). In other embodiments, the ratio of buffer to lecithin is not less than about 1:1. In other embodiments, the ratio of buffer to lecithin is about 2.5:1. In still other embodiments, the ratio of buffer to lecithin is not less than about 5:1.

In other embodiments, the disclosed triglyceride-lecithin compositions are stabilized with respect to microbial exposure by inclusion a preservative, such as benzoic acid/sodium benzoate or potassium sorbate, and/or adjusting the final pH of the composition to be in the "acid food" range, i.e. at or below pH 4.5. In certain instances, an additive such as a polysorbate may be employed with the effect of stabilizing the composition to chemical and/or physical degradation or of changing the organoleptic properties of the composition.

The compositions of certain embodiments of the present invention are palatable and may be enjoyed as still or carbonated flavored beverages. As compounded and produced by the method described below and in U.S. patent application Ser. No. 13/135,057 (the entire content of which has been incorporated herein by reference), the presently disclosed compositions are substantially free of the taste and unpleasant oily mouthfeel associated with typical plant based oils such as corn oil. They offer the advantage of consumer acceptance, and substantially eliminating the reluctance to consume based on taste and mouthfeel. The acceptable and not unpleasant mouthfeel of the disclosed compositions can lead to better compliance with any weight control regimen involving routine consumption of any of the disclosed compositions.

As discussed above, compositions according to embodiments of the present invention include lecithin and a triglyceride source dispersed in the lecithin, as well as conditioned water. In certain embodiments of the present invention, the lecithin and conditioned water form a hydrated lecithin carrier vesicle (HLCV) composition including the lecithin, which can have a phosphatidylcholine content of at most about 80 w/w % and the conditioned water. The conditioned water hydrates the lecithin to form an HLCV. In some embodiments, the HLCV may have at least one active ingredient dispersed therein. However, in some embodiments, the HLCV composition includes alcohol which can help form HLCV dispersions of the active ingredient and ensure proper hydration in the conditioned water. In other embodiments, the HLCV composition further includes one or more stabilizing agents. In some embodiments, the active ingredient is solubilized in lecithin with or without alcohol in a homogeneous liquid mixture. Other embodiments of the present invention are directed to methods of making the HLCV compositions and homogeneous mixtures.

In other embodiments of the present invention, a hydrated lecithin carrier vesicle (HLCV) composition consists essentially of a vesicle having a membrane and an aqueous phase, and conditioned water. In these embodiments, the term "consists essentially of" refers to the general absence from the composition of lecithin particles and lecithin-based particles (or nanoparticles) that are not vesicles, within the meaning of that term as defined below. However, these embodiments include the same vesicles as the embodiments described above and below, and can be made by any of the methods described below. Also, these embodiments can further include any of the below described active ingredients and/or other components (e.g., stabilizing agents, alcohols and/or oils). Indeed, other than generally excluding the presence in the compositions of non-vesicle lecithin-based materials (e.g., non-vesicle lecithin particles and nanoparticles, and/or nanocrystals of active ingredient that are coated with non-vesicle lecithin), these embodiments may have the same composition as the embodiments described above and below (e.g., they may be made using the same materials and methods, and may include the same active ingredients, and other components, such as alcohols, stabilizing agents, oils, etc.).

The use of lecithin to disperse active ingredients, according to this disclosure, has utility for compounds to be ingested and is also of utility in many other areas including, without limitation, the fields of agriculture, horticulture, nutraceuticals, pharmaceuticals (for the diagnosis, treatment and palliation of disease), cosmetics and personal care products, fragrances and color agents, environmental remediation, inorganic and composite materials, paints and inks, catalysis, and such other fields where a low cost natural dispersing agent is desirable. In all embodiments of this invention, it is contemplated that other agents, including water-soluble substances, may optionally be added to the hydrated lecithin carrier vesicle dispersions to enhance their suitability for use in a given application, for example addition of a water-soluble anti-oxidant such as ascorbic acid to improve shelf-life of a nutrition product. Selection of the specific additives will be obvious to those of ordinary skill in the art.

Embodiments of this invention provide for the use of bulk food or industrial grade lecithin to solubilize water-insoluble and partially water-insoluble substances in a manner that is cost-effective for broad use in consumer products, including food, beverage and nutritional supplements, and in other applications where effective commercialization is dependent on the cost of raw materials that precludes the use of high PC lecithin (i.e. lecithin having more than 80 w/w % phosphatidylcholine).

Lecithin is usually prepared from oil-bearing seeds used for food, especially soybeans; but may also be prepared from animal sources. As used herein, lecithin is defined as a complex mixture obtained from animal and plant sources by hydration of solvent-extract oils, as defined in the Joint World Health Organization/United Nations Food Safety Agency Evaluation Committee for Food Additives (JECFA), (Food and Agriculture Organization of the United Nations, Food and Nutrition Paper 52, "Compendium of Food Additive Specifications" (FNP 52), Addendum 2 (1993)), which is incorporated herein by reference in its entirety. Specifically, the JECFA Compendium of Food Additive Specifications provides the following definition of "Lecithin": "Usually prepared from oil-bearing seeds used for food, especially soybeans; may also be prepared from animal sources; a complex mixture of acetone-insoluble phosphatides which consists chiefly of phosphatidyl-choline, phosphatidyl-ethanolamine, and phosphatidyl-inositol, combined with various amounts of other substances such as triglycerides, fatty acids, and carbohydrates; refined grades may contain any of these components in varying proportions and combinations depending on the type of fractionation sed; its oil-free forms, the preponderance of triglycerides and fatty acids is removed and the product contains 90% or more of phosphatides representing all or certain fractions of the total phosphatide complex." This complex mixture comprises acetone-insoluble phosphatides including predominantly phosphatidylcholine, phosphatidylethanolamine, and phosphatidylinositol, as well as smaller amounts of triglycerides, fatty acids, and carbohydrates; refined grades may contain any of these components in varying proportions and combinations depending on the type of fractionation used; its oil-free forms, the preponderance of triglycerides and fatty acids is removed and the product contains 90% or more of phosphatides representing all or certain fractions of the total phosphatide complex.

As used herein, vesicle is defined as a composition having a membrane-forming lipid component and an aqueous phase. In some embodiments, the membrane-forming lipid component is a phospholipid bilayer membrane.

As used herein, active ingredient refers to any compound that is selected to be and is capable of being incorporated into the vesicle. For example, in some embodiments, the active ingredient can be lipophilic which includes many amphiphilic compounds, as discussed below. Lipophilic compounds are more soluble in fats, oils, lipids and organic solvents such as ethanol, methanol, ethyl ether, acetone, chloroform and benzene than in water. Within their structure, lipophilic compounds may contain hydrophilic moieties, such as the hydroxyl group in sterols and the carboxylic acid group in long chain fatty acids. In some embodiments, lipophilic compounds are incorporated with the membrane-forming lipid component of the vesicle. In some embodiments, lipophilic compounds have log P values in a range from about 0 to about 8, where the higher log P value corresponds to increased lipophilicity. In some other embodiments, the lipophilic active ingredient has a log P value range from about 2 to about 7.

As used herein, the term "lipophilic compounds" and "lipophilic active ingredient" are used interchangeably, and refer to compounds having greater solubility in organic solvents, fats and oils, than in water. The term "lipophilic" also encompasses many amphiphilic compounds, which include compounds having both hydrophobic and hydrophilic regions. Indeed, molecules may contain water-loving (hydrophilic) moieties, such as the hydroxyl group in sterols and the carboxylic acid group in long chain fatty acids. This is true for many (biologically) active species for which embodiments of this invention provides compositions and methods for aqueous dispersion formation. In such cases the molecules may also be described as amphiphilic. The methods and compositions of certain embodiments of this invention encompass entities that may be so described and that can be dispersed in hydrated lecithin vesicle bilayers; some embodiments are shown in the examples. In general, amphiphilic molecules are arranged in both portions of the bilayer, with their hydrophilic portions associated with the polar surface and the hydrophobic portions directed to the acyl chains of the phospholipids in the bilayer interior.

As used herein, dispersion refers to a lecithin-based phase generally uniformly distributed in the bulk aqueous solution. Further, as used herein, the dispersion is stable if it does not suffer from physical instability manifested by visible phase separation, such as when the vesicles aggregate and separate by precipitation or creaming (i.e. aggregates fall to the bottom or rise to the top of the mixture, respectively) or when the incorporated lipophilic materials separate from the vesicles and form visible aggregates. That is, in a stable dispersion of HLCV without an active ingredient, substantially all of the vesicles in the dispersion are distributed without visible clumping. For a stable composition including an active ingredient, in addition to the vesicle stability discussed above, the active ingredient remains properly associated with the vesicles. For example, if a lipophilic compound is incorporated in an HLCV dispersion, the hydrophobic regions of the lipophilic compound are associated with (in contact with) the non-polar regions of the phospholipid vesicle membrane. For a composition including lipophilic compounds having hydrophilic moieties incorporated in an HLCV dispersion, the hydrophilic regions of the lipophilic compounds are associated with the polar regions and the hydrophobic regions are associated with the non-polar regions of the phospholipid vesicle membrane. As such, a stable HLCV having an incorporated active ingredient also means that substantially all of the active ingredient present in the composition is incorporated into/associated with the vesicle membrane. The vesicle carrier having an active ingredient in its membrane is also referred to as a "loaded" carrier vesicle, and refers specifically to the active ingredient being incorporated in the phospholipid membrane of the vesicle to stabilize the compound from aggregation or degradation in the bulk aqueous solution. Accordingly, the active ingredient incorporated in the phospholipid membrane environment, and so dispersed in an aqueous medium, is stabilized in other environments (e.g., food, beverages, gastro-intestinal or digestive tract).

As used herein, conditioned water is defined as water that has less than 100 ppm hard ions, and in some embodiments less than 60 ppm hard ions. Hard ions cause hardness in water, and the free hard ions commonly found in water are calcium and magnesium ions. Conditioned water refers to water having a reduced level of free hard ions whether the water has a reduced level without treatment (i.e. "soft" water) or if treatment is required. Hardness is measured by an EDTA titration method such as that described in ASTM method D1126 "Standard Test Method for Hardness in Water," the entire content of which is incorporated herein by reference. The treatment to reduce hardness may include chelation. Naturally soft water, (i.e., water having hardness less than about 100 ppm of hard ions), is considered to be conditioned water for the purposes of this disclosure. In some embodiments, the water is substantially free of buffer ions and in other embodiments, the water has been purified by distillation, deionization, reverse osmosis or a similar technique such that the conductivity is less than 20 microSiemens per centimeter. Buffer ions are those that resist changes in their pH, for example phosphate, citrate, acetate and tris(hydroxymethyl)methylamino ions. Embodiments of the present invention recognize that the quality of the water has an effect on the final dispersion and stability of the lecithin vesicles. Compositions having unstable vesicles and/or vesicles (even if stable) having a broad or skewed size distribution can result in cloudy (turbid) dispersions. Accordingly, though the addition or presence of stabilizing agents is not necessary, in the absence of stabilizing agents, the likelihood of the HLCVs to cause whitening is inversely dependent on water purity—i.e., as water purity increases, the likelihood of whitening decreases.

Hydrated Lecithin Carrier Vesicles (HLCVs)

Embodiments of the present invention are directed to hydrated lecithin carrier vesicles in which one or more active ingredients are incorporated. The HLCVs are prepared using lecithin having a low PC content and conditioned water (CW). In some embodiments, a HLCV is prepared using lecithin having a triglyceride source incorporated therein.

Lecithin Having Low PC Content

The lecithin used to make the HLCVs has a low PC content. As used herein, lecithin having a low PC content means a lecithin ranging from non-deoiled (crude) lecithin to lecithin having a phosphatidylcholine content of approximately 80 w/w % or less. Indeed, in some embodiments, the lecithin has a PC content of less than, but not including 80 w/w %. For example, the HLCV dispersion can be prepared from known food-grade materials that are acceptable for consumption, including those listed as Generally Regarded As Safe (GRAS) by the US Food and Drug Administration. Accordingly, embodiments of the present invention have food-grade lecithin for which the phosphatidylcholine content is from about 20 to about 80 w/w %. In other embodiments, the lecithin has a phosphatidylcholine content from about 20 to about 70 w/w %. In other embodiments, the lecithin has a phosphatidylcholine content from about 20 to about 60 w/w %. In other embodiments, the lecithin has a phosphatidylcholine content from about 20 to about 50 w/w %. In other embodiments, the lecithin has a phosphatidylcholine content from about 20 to about 40 w/w %. In other embodiments, the lecithin has a phosphatidylcholine content from about 20 to about 30 w/w %. In some embodiments, lecithin that has not been de-oiled is used, for which the phosphatidylcholine content is from about 20 to about 25 w/w %.

Active Ingredient

Non-limiting examples of lipophilic active ingredients include: olfactants, such as natural and synthetic fragrances and essential oils (which are described in more detail below); flavor compounds and taste modifiers, such as natural essences and essential oils, for example from apple, orange and lemon, (including combinations of such compounds with carrier oils); coloring agents, such as porphyrin based macrocycles; plant oils, including olive oils, flax oils, almond oils, canola oils, and corn oils; vitamins, such as vitamins A, D, E, and K and their pharmacologically active metabolites, salts and compounds, for example vitamin D, vitamin E acetate and vitamin A palmitate; phytochemicals, such as plant sterols and essential oils, for example beta-sitosterol, isoflavones, curcuminoids, and polyphenolic compounds; oil soluble acids and alcohols, such as lactylic acid and triglycerides having fatty acids, as well as essential fatty acids alone, for example linoleic and linolenic acids, eicosapentaenoic acid (EPA) (20:5 n−3) and docosahexaenoic acid (DHA) (22:6 n−3) and their natural sources, such as evening primrose oil, safflower oil and fish oil; drugs such as cyclosporin A, propofol, fat soluble protease inhibitor antiretroviral drugs, antibiotics and lipophilic members of other drug classes; carotenoids, such as beta-carotene and lycopene; steroidal hormones, such as estrogens, estradiols, and cortisones; flavonoids, such as resveratrol; proteins, enzymes, coenzymes and numerous other lipophilic biologically active compounds. It is obvious, however, to those of ordinary skill in the art, that the compounds are not limited to particular classes of lipophilic ingredients of foods, beverages, medicines and nutritional supplements.

As used herein, an essential oil is a concentrated, hydrophobic liquid containing volatile aroma compounds from plants. Essential oils do not necessarily as a group have specific chemical properties in common beyond conveying characteristic fragrances. They are well known for their use as olfactants and flavoring agents and find wide utility in traditional medicine. (Traditional medicine, as defined by the World Health organization, refers to the knowledge, skills and practices based on the theories, beliefs and experiences indigenous to different cultures, used in the maintenance of health and in the prevention, diagnosis, improvement or treatment of physical and mental illness).

Alcohol

In some embodiments, the HLCV composition includes alcohol. In some embodiments, alcohol is added to the conditioned water for hydration of the lecithin to form the HLCVs. In other embodiments, if the active ingredient is not easily solubilized in the lecithin composition, the addition of alcohol can improve solubilization of the active ingredient in the homogeneous liquid mixture. According to embodiments of the present invention, the alcohol is a short chain alcohol. Examples of short chain alcohols include methanol, ethanol, isomers of propanol, and isomers of butanol. The amount of alcohol needed to facilitate solubilizing the active ingredient will vary depending on the type of alcohol and the particular active ingredient, and can be determined empirically by a person having ordinary skill in the art.

In some embodiments, the alcohol added to help dissolve the active ingredient in the lecithin to form a homogenous liquid mixture, is provided in a range from about 5 to about 50% alcohol by weight relative to the combined weight of the lecithin and the active ingredient. The addition of alcohol to the lecithin and active ingredient composition may be with or without heating, and with or without the addition of oil, as discussed herein.

In some embodiments, alcohol is added to the conditioned water for the hydration of lecithin. In some embodiments, the additional alcohol is an aliphatic short chain alcohol (e.g., methanol, ethanol, propanol, or butanol). The amount of alcohol can vary and will depend on the properties of the active ingredient(s). For example, for the hydration of lecithin, up to a total of 40% v/v of an alcohol can be present in the HLCV composition.

In some embodiments, the dispersion may be dried by standard industrial methods for example to a powder, granule or cake form.

Stabilizing Agents

In other embodiments of the invention, the HLCV compositions further include at least one stabilizing agent. Non-limiting examples of stabilizing agents include polysorbate (polyoxyethylene sorbitan monoesters), polyoxyethylene alkyl ethers (PAEs), and the like. The addition of a stabilizing agent is optional and will generally depend on the properties of the active ingredient(s) to be dispersed in the HLCVs. For some applications, addition of a polysorbate or PAE may increase stability. As such, the need for polysorbate or PAEs can be determined empirically by those of ordinary skill in the art.

As used herein, the term polysorbates includes the class of emulsifiers which are oily liquids derived from polyoxyethylene derivatized sorbitan (a derivative of sorbitol) monoesterified with fatty acids. The PAE class of molecules is suitable for use in applications not involving ingestion of the HLCVs. It is readily apparent to those of ordinary skill in the art that, for applications not involving ingestion, a suitable PAE may be substituted for polysorbate in the methods and compositions described herein that include and/or employ polysorbates.

The polysorbate-containing HLCVs of embodiments of the present invention do not have a detectable bitter taste and are physically stable to dilution, pasteurization and storage in water, many juices and other beverages, as demonstrated by retention of clarity. The following polysorbates are non-limiting examples that can be used: polyoxyethylene (20) sorbitan monooleate, polyoxyethylene(20) sorbitan monolaurate, polyoxyethylene(20) monopalmitate, and monostearate. In some embodiments, polyoxyethylene(20) sorbitan monooleate (i.e., polysorbate 80), or polyoxyethylene(20) sorbitan monolaurate are used. An effective amount of polysorbate can be determined using known methods. In some embodiments, for example, polysorbate is used at a molar ratio of polysorbate to lecithin of between about 1:3 and about 1:20. In other embodiments, polysorbate is used at a molar ratio of between about 1:5 and 1:10. In other embodiments, polysorbate is used at a molar ratio of between about 1:7 and 1:9. For the purpose of determining the molar ratio, the molecular weight of the lecithin is to be assumed to be 800.

Methods of Preparing HLCV

Embodiments of the present invention are directed to methods of preparing hydrated lecithin carrier vesicles (HLCVs). In some embodiments, HLCVs with at least one active ingredient loaded therein are prepared without the use of any organic solvents, alcohols or otherwise. However, in some embodiments, alcohols may be used to facilitate making the HLCVs although other/additional organic solvents are not required or used. In some embodiments of the present invention, a method of forming an HLCV composition includes hydrating and processing lecithin having a low PC content in conditioned water followed by the addition of at least one active ingredient. In other embodiments of the present invention, the active ingredient may be mixed with low PC content lecithin and an alcohol, together with minimal water, to form a homogenous liquid phase (without forming vesicles), followed by hydration and processing which forms dispersed vesicles. In other aspects, methods of forming HLCV compositions having an active ingredient dispersed therein include using lecithin having a high PC content (i.e., greater than 80 w/w % phosphatidylcholine) in conditioned water.

Hydration of Lecithin

In some embodiments, lecithin having a low phosphatidylcholine content is hydrated upon exposure to conditioned water to form hydrated lecithin carrier vesicles dispersed in CW. In some embodiments of the invention, the lecithin is hydrated with enough conditioned water to effectively perform a processing step (e.g. homogenization, sonication, microfluidization, high shear mixing, etc.). Indeed, the HLCV dispersions contain, by weight, at least as much conditioned water as lecithin, (i.e. a ratio of CW to lecithin of at least 1:1), prior to any drying or further compounding steps. In some embodiments, for example, lecithin may be hydrated with 3 parts water to 1 part lecithin (by weight). In other embodiments, lecithin may be hydrated with up to 4 parts water to 1 part lecithin, or 5 parts water to 1 part lecithin, by weight. In other embodiments, lecithin may be hydrated with greater than 5 parts water to 1 part lecithin. In these embodiments, the relative amounts of CW and lecithin are relative to the lecithin alone.

In other embodiments, lecithin is hydrated in the presence of at least one active ingredient. In these embodiments, the ratio of lecithin to active ingredient is at least 1:1 and may, in general, be up to about 5:1 by weight. However, there is no particular upper limit to this ratio other than imposed by commercial or practical processing constraints obvious to those of ordinary skill in the art. In these embodiments, the conditioned water is provided at a ratio of CW to the sum of lecithin and active ingredient ranging from about 3:1 to about 5:1, by weight. This is necessary as the active ingredient can be provided up to about a 1:1 ratio with the lecithin. For example, when the total weight of lecithin and active ingredient is 200 to 250 mg (lecithin+active ingredient), the amount of CW could be 1 ml (1000 mg). It is apparent to those of ordinary skill in the art that the amount of conditioned water with respect to the lecithin or lecithin and active ingredient, is, in general, only limited by the desired concentration of HLCV composition and active ingredient with respect to any further production or manufacturing steps for the final desired application of the composition.

Loading of Active Ingredient in HLCVs

In some embodiments, HLCV compositions are prepared, (i.e., lecithin is hydrated and then processed) to form dispersed vesicles prior to the addition of at least one active ingredient. These methods of forming HLCVs prior to loading the active ingredient(s) are most effective when the active ingredient is a liquid (e.g., is in liquid form at a temperatures up to the boiling point of the conditioned water or the boiling point of the conditioned water and alcohol mixture), so that the active ingredient is easily solubilized in the hydrated lecithin vesicle composition. These methods of adding the active ingredient after processing (i.e., to pre-formed vesicles) are particularly suitable for such ingredients as essential oils, lipophilic flavor compounds, and flavor compound mixtures having lipophilic components. This method is most effective for HLCVs that have been processed (e.g. by homogenization or high shear mixing) to form UVs prior to loading. Accordingly, if the active ingredient can be incorporated in the hydrated lecithin composition, then the active ingredient can be added to "pre-formed" lecithin vesicles. As discussed above, solubility of the active ingredients may require the addition of alcohol, heating, or any combination of these. It is apparent to those of ordinary skill in the art that an active ingredient having a low solubility, if added in a small amount would slowly be incorporated in the vesicle composition over time. It is also known to those of ordinary skill in the art that the extent of incorporation in the dispersed HLCVs is dependent on both the rate at which the active dissolves in the aqueous phase and time. Without the aid of alcohol, or heating, an active ingredient having a log Kow (i.e., an octanol:water partition coefficient) of less than about 4.5, will not likely be incorporated within a reasonable amount of time. However, active ingredients having a log Kow of 4.5 or greater could be incorporated more rapidly. Solubility of such active ingredients, including as enhanced by heat and/or alcohol, can be determined empirically by those of ordinary skill in the art.

A stabilizing agent can be added to the lecithin composition prior to or after processing. In some embodiments, a stabilizing agent is added to the HLCV composition after processing. In other embodiments, a mixture of lecithin and a stabilizing agent is hydrated in CW prior to processing.

Following addition of the active ingredient to the HLCVs, the mixture is processed by high shear mixing or homogenization to form a dispersed composition of HLCVs having an active ingredient incorporated therein.

Transparency

In some embodiments, the size distribution of the lecithin carrier dispersion can be manipulated such that the dispersion is essentially optically clear (i.e. transparent). For the purpose of describing embodiments of the invention herein, the mean diameter of dispersion particles and structures in the submicron range (<1 µm) is defined as the volume weighted mean diameter, generally of a unimodal distribution of sizes. The volume weighted mean diameter of the vesicles can be determined by any known technique. For example, the volume weighted mean diameter is determined using electron microscopy or dynamic light scattering. Upon determining the mean vesicle size, the vesicles can be reduced in size using standard methods well known in the art, including without limitation: sonication, microfluidization and high pressure homogenization.

In some embodiments, a lecithin carrier vesicle having an active ingredient therein and prepared by a method of according to embodiments of the present invention, remains clear (or, transparent) in dispersion. Clarity refers to transparency rather than translucency. This transparency is achieved by producing a dispersion wherein the mean diameter of the particles is about 0.12 µm or less, preferably less than 0.10 µm, and more preferably less than 0.08 µm. Additionally, the distribution of sizes includes few particles of larger diameters that cause cloudiness, which may manifest as whitening. For the purpose of describing certain embodiments of this invention, the presence of such larger particles may be quantitated by the cloudiness or haziness, hereafter referred to as turbidity. Transparent dispersions are those with low turbidity. The quantitation of such turbidity may be performed, for example, using a nephelometer. Turbidity of dispersions may be expressed relative to standards of known turbidity. The turbidity caused by scattering of light by submicroscopic particles, even those with diameters significantly smaller than the wavelength of the light, is a complicated function of many variables including both the particle size and the wavelength. In general, the presence of larger particles, i.e. those that cause turbidity (whitening, cloudiness, haziness), is revealed by scattering at longer wavelengths. This scattering of light results in the observed turbidity (i.e., lack of clarity) of aqueous dispersions. A quantitative measure of relative turbidity is the relative absorbance at 800, 860 and/or 900 nm as measured using a conventional UV/visible spectrometer. Turbidity caused by instability of the dispersions is thus readily quantitated by spectrophotometric methods in the desired range.

While HLCV compositions with or without dispersed active ingredients may desirably be transparent or nearly so, transparency is not a requirement of any embodiment of the present invention. For example, if the composition is intended to be added to a food product, its clarity in solution is typically not relevant, and therefore it may not be necessary to reduce the vesicle size. However, if the composition is intended to be added to a transparent or semi-transparent drink, for example, the cloudiness or turbidity may desirably be adjusted to meet consumer expectations.

Homogeneous Liquid Mixture

In some embodiments, the active ingredient is added to the lecithin prior to hydration. In these embodiments, the active ingredient may be dissolved at room temperature in the lecithin based mixture, which may also include alcohol and may also include a minimal amount of conditioned water and/or an oil. In some embodiments, the weight amount of lecithin in the homogenous liquid mixture is greater than any other single component of the homogenous liquid mixture. That is, while the lecithin may not be more abundant than all other components combined, it is provided in an amount that is more than any other single component. In this way, lecithin may be used as a solvent for the homogenous liquid mixture. Some active ingredients may more readily solubilize with heating. In some embodiments, therefore, the active ingredient is mixed with lecithin, and may include alcohol, a minimal amount of alcohol, oil, and may be mixed at an elevated temperature. For example, the heating temperature is selected from a range of about 60° C. to about 80° C. The desired temperature may be determined by one of ordinary skill in the art with consideration of the properties of the active ingredient and the components of the composition. For example, the heating temperature should not exceed the boiling point of the composition which is dictated by the various components of the composition. As would be understood by those of ordinary skill in the art, the heating temperature should not exceed the boiling point of the component of the composition which has the lowest boiling point. For example, if alcohol is present in the lecithin composition, then the highest desired heating temperature should not exceed the boiling point of the alcohol (which in general will be the component with the lowest boiling point). In some embodiments, lecithin and at least one active ingredient are first dissolved in a homogenous liquid mixture prior to vesicle formation.

By way of example, plant phytosterols have a melting temperature above 100° C. (e.g. beta-sitosterol has $T_{mp}$ of 136 to 140° C.), and therefore, plant phytosterols are not effectively incorporated into the HLCV composition after the vesicles are formed. Accordingly, in some embodiments of the present invention, a composition having at least one active ingredient dispersed therein, is prepared by first dissolving the active ingredient together with lecithin to form a single phase homogenous liquid mixture. In some embodiments, alcohol is added to help solubilize the active ingredient in the lecithin. In some embodiments, up to about 50% alcohol (by weight with respect to lecithin) is added to the lecithin and active ingredient mixture. As discussed, in some embodiments, a minimal amount of conditioned water may be added to aid in the solubilization of the active ingredient in the lecithin and alcohol mixture. For example, no more than 10% by weight (w/w) conditioned water relative to the weight of lecithin may be added. It is apparent to those of ordinary skill in the art that an excess of water will prevent the formation of a single phase. To further promote the formation of a homogeneous liquid mixture with the lecithin, the active ingredient may first be dissolved in an oil (with heating if necessary).

In some embodiments, the active ingredient may first be dissolved in an oil in order to facilitate solubilization in the lecithin to form the homogenous liquid mixture. For example, an active ingredient may first be dissolved in a non-polar, hydrophobic carrier substance, such as a natural oil, and then mixed with the HLCV composition. Dissolution of the active ingredient in oil may also be combined with heating and/or the addition of alcohol. Examples of an oil include extracted triglyceride seed oils from plants, such as soy, corn, olive, sunflower, canola, olive. Oils also include animal oils such as fish or krill, as well as essential oils. Essential oils include, without limitation, oils of: citronella, clove leaf, eucalyptus, grapefruit, lemon, lime, mentha arvensis/mint, orange, oregano, peppermint, spearmint, star anise, tangerine, tea tree, thyme and wintergreen, and the embodiments include the use of the primary chemical components of these oils, such as thymol, carvacrol, limonene, menthol, carvone, methyl salicylate, cineole, citranal, pinene, and terpinen-4-ol.

The homogeneous liquid mixture is then hydrated with mixing in CW to form vesicles. In some embodiments, a short chain alcohol is added to the CW, i.e., if the short chain alcohol is not already present in a sufficient amount in the lecithin containing mixture. A sufficient amount of short chain alcohol is no less than that which provides a final lecithin hydrating solution concentration of at least about 5 v/v % alcohol, and no more than about 40 v/v %. In some embodiments, the final lecithin hydrating solution concentration of alcohol is from about 20% v/v to about 30% v/v. The lecithin hydration is performed at a temperature that maintains the homogeneous liquid mixture with lecithin in a fluid state.

After formation of the HLCVs by hydration, the HLCVs are processed by homogenization or high shear mixing to form a dispersion of the active ingredient incorporated in the HLCV composition.

HLCVs from Lecithin Having a High PC Content

In further embodiments of the invention, a method of producing an HLCV composition uses lecithin having a high PC content (i.e. lecithin having a phosphatidylcholine content of more than 80% w/w). In this method, high PC content lecithin (or alternatively, substantially pure phosphatidylcholine) is mixed with an active ingredient following one of the methods disclosed herein for solubilization of active ingredients in low PC content lecithin. The methods and intermediate compositions described herein for adding an active ingredient after hydration and processing, or by forming a homogenous liquid mixture prior to hydration and processing, are also applicable to the preparation of HLCVs using high PC content lecithin. Such HLCVs are suitable for uses in pharmaceutical applications. Indeed, in these embodiments, the lecithin has a higher PC content such that it is acceptable for pharmaceutical use. For example, in these embodiments, the HLCVs have 90 w/w % or greater PC by weight for an inhaled or injectable product.

Other purified phospholipids may be added as required for the desired in vivo performance of the formulation. In some embodiments, a pharmaceutically acceptable formulation of propofol for parenteral use may be made by hydrating an alcoholic mixture of phosphatidylcholine and phosphatidylglycerol in conditioned water, followed by homogenization with a high pressure homogenizer, and then incubation with propofol.

Optionally, a pharmaceutically acceptable stabilizing agent, such as polysorbate, may be added during hydration or after processing. The organic solvent-free processing method disclosed herein for lecithin is also applicable for pharmaceutically acceptable phosphatidylcholine. The alternative method, based on a homogeneous liquid mixture of lecithin and other ingredients, may be used with those pharmaceutically active ingredients that are soluble in the phosphatidylcholine-alcohol mixtures corresponding to those described with respect to the low PC content lecithin embodiments, with the addition of a small amount of conditioned water (up to 10% w/w relative to phospholipids) as required to generate a homogeneous liquid mixture. As described herein, the active ingredient may first be dissolved, with heating if necessary, in a pharmaceutically acceptable oil, such as a triglyceride ester of fatty acids (wherein the fatty acids may be the same or mixed).

Further Processing, Purification

Following formation of the HLCVs the composition can be further processed as desired. For example, to reduce the vesicle size, the dispersion can be subjected to high shear mixing or high-pressure homogenization. The energy required for size reduction is reduced by the presence of alcohol, compared to the corresponding size reduction process performed, if feasible, on the same components in the absence of alcohol. The lower energy processing is of commercial benefit resulting in lower process energy costs and the ability to use a wider range of processing equipment. For example, with alcohol present, a greater degree of size reduction can be achieved for a given energy input; in some cases this enables production of an optically clear presentation of HLCVs whereas such optical clarity may not be achievable in the absence of the alcohol.

The HLCV compositions as disclosed herein can be dried to a solid form, for example to a powder, flake or cake, by any standard industrial drying method, such as spray drying or freeze drying, and alternatively or subsequently incorporated into a paste or cream. Additional further processing steps may include: adjusting the pH of the composition, addition of preservatives or antimicrobial agents, or the addition of flavors to enhance the taste of the composition.

In some embodiments, it may be advantageous to blend hydrated triglyceride-lecithin dispersions having different entrapped compositions, some of which may be the exemplary compositions as described above, in order to obtain a combination of immediate and delayed action or other desirable properties.

All the above compositions and blends may be prepared with or without other agents such as proteins, peptides, carbohydrates, fiber, dietary supplements, drugs or other active agents.

Applications

The HLCV dispersions according to embodiments of the present invention are essentially free of non-dispersed active ingredients (i.e., once dispersed in the HLCV composition, the active ingredients remain substantially dispersed and do not precipitate out of the dispersion to any significant degree). In some embodiments, the lecithin vesicle compositions are distinct from nanoemulsions and from dispersions of non-bilayer solid nanoparticles stabilized by a surface active agent (such as lecithin).

The compositions, intermediate solutions, and methods for production, of certain embodiments of this invention provide for aqueous based dispersions of water-insoluble materials using relatively inexpensive food-grade lecithins, specifically lecithin having a PC content of less than about 80% by weight.

Though not limited to any applications, the HLCVs according to certain embodiments of the present invention may be used to make substantially clear aqueous dispersions of fat-soluble active ingredients that may be used in beverages or nutritional supplements, as the dispersions are physically stable to dilution, pasteurization and storage in water, juices and other beverages. The fat-soluble ingredients can include antioxidants (for example, vitamin E). The dispersion can be concentrated and dried to a powder and rehydrated as required by the desired application. The compositions and methods of embodiments of the invention also disclose use of food grade materials, for example, those that have already been qualified in an application as Generally Regarded As Safe by the US Food and Drug Administration.

The HLCV compositions of certain embodiments of this invention can be processed using conventional equipment that is widely employed in the food and beverage industry. The components of the hydrated lecithin carrier vesicles are relatively inexpensive. In addition, the loading of the food/beverage/nutritional supplement ingredient into the carrier can be elevated to levels that yield cost effective formulations for use in relevant consumer and other products.

The HLCV dispersions of certain embodiments of the present invention effectively behave as true solutions and may be, or may be employed in the preparation of, products that are to be consumed orally or otherwise introduced into the oral cavity. A particular benefit of some of the compositions of embodiments of this invention is that they provide aqueous dispersions that are essentially optically clear as used in final products, and maintain that clarity with storage, with addition to some juices and other beverages, and with exposure to high temperature, as during pasteurization. In some embodiments, the lecithin-based matrix also provides enhanced chemical stability of the water-insoluble materials, e.g., resistance to oxidation, and can inhibit undesirable odors and taste, and poor mouth feel of these materials. Certain lipids are themselves considered to be food or nutritional supplement ingredients of choice, for example phosphatidylcholine and, especially, lipids derived from marine organisms, such as krill. It is clear that the HLCVs, intermediates, and methods of preparation described herein, may optionally employ these lipids.

Specific mixtures of triglycerides, and combinations thereof with other additives including, protein, hydrolyzed protein, peptides, enzymes, carbohydrates, artificial sweeteners etc are particularly beneficial for certain medical conditions. These compositions may be augmented with other dietary supplements in order to achieve a desired health benefit. With respect to satiety, in combination with other agents known to produce satiety, the present compositions can produce a surprisingly synergistic effect, e.g. with the incorporation of a relatively small amount of partially hydrolyzed guar gum. For the goal of weight control, a composition with a low calorie artificial sweetener rather than sucrose, high fructose corn syrup or other natural sweetener is preferable. Similarly, for such an application, it is desirable to minimize the calories from fat in the composition itself by minimizing the total amount of triglyceride while retaining the desired satiety effect. In certain instances, particularly to improve the nutrition uptake for persons in whom such uptake is impaired, for example by anatomical, physiological or digestive tolerance issues, a higher content of triglyceride—and other components—may be desired.

While the triglyceride-lecithin compositions of certain embodiments of the invention can be prepared from a wide range of triglycerides, such as natural oils, an average composition of triglyceride as defined by the acyl chain profile (i.e., the content of mono-unsaturated fatty acid, di-unsaturated fatty acid and polyunsaturated fatty acids relative to saturated fatty acids) includes an overall ratio of unsaturated to saturated fatty acids of at least 4:1. In some embodiments, the (monounsaturated) oleic and (tri-unsaturated) alpha-linolenic fatty acids relative to (di-unsaturated) fatty acids in the triglyceride of the disclosed composition is at least 1:1. In some embodiments, the average oleic acid content of the triglyceride in the triglyceride-lecithin compositions is at least 40% by weight of all the fatty acids. Examples include mixtures of corn oil with olive oil and with canola oil.

In users having cardiovascular risks, triglyceride-lecithin compositions without any fatty acid chains less than C14 (14 carbons in length) and without any fully saturated carbon chains may be desired, as these are considered to be possibly harmful to cardiovascular health irrespective of their ability to produce satiety in users. In yet other applications, the presence of these particular short and/or fully saturated acyl chains may be advantageous.

In some embodiments, the triglyceride-lecithin composition has conjugated linoleic acid substituted for oleic and/or linoleic acid.

As discussed herein, hydrolysis products of triglycerides may also be incorporated in the compositions of certain embodiments of the present invention at levels that do not destabilize the overall composition in the stomach so as to cause loss of activity. Such hydrolysis products include free fatty acids and mono- and di-acylglycerides. However, fully saturated and trans-unsaturated fatty acids, free or as glyceride acyl chains, are in some instances less desirable than cis-monounsaturated and polyunsaturated fatty acids with chain lengths between 14 and 18 carbons.

Incorporation of active substances in the disclosed triglyceride-lecithin mixtures is also contemplated, including when a therapeutic effect is desired. For example, fat soluble vitamins (such as vitamins A, D, E and K), essential fatty acids (such as EPA and DHA), esters or triglycerides, and lipophilic drug substances, are suitable for inclusion in the lecithin:triglyceride mixtures of embodiments of the present invention. This latter category includes the water insoluble active moieties of drugs wherein solubility and bioavailability have heretofore been achieved by formation of salts or derivatives, with hydrophilic counter-ions or non-active functional groups, respectively. Equally, water-soluble materials can be dissolved within the aqueous phase of the compositions for co-delivery. Particular triglyceride compositions will enhance particular lipid soluble active uptake.

Without being bound to a particular theory for the basis of the activity, the present compositions are believed to enable rapid and highly efficient enzymatic hydrolysis of triglycerides in the duodenum by pancreatic enzymes. Compositions of the present invention provide for presentation of the triglyceride ester linkages homogeneously dispersed within a phospholipid matrix. This presentation occurs at the phospholipid water interface, and possibly with endogenous bile salts from the gall bladder, thereby possibly mimicking the environment that is normally produced with bicarbonate, phospholipid, and bile salts.

Transport of the active ingredients into the bloodstream occurs by normal mechanisms and yields more rapid and/or extensive bioavailability than the same molecules not formulated in the HLCVs.

For triglyceride fats, duodenal enzymatic hydrolysis yields free fatty acids and monoacyl glycerols that are taken up by cells lining the small intestine (enterocytes). For medium and long chain fatty acids, these molecules are taken up from micelles and liposomes are then repackaged intracellularly as chylomicrons for delivery via interstitial fluid and the lymph to the bloodstream. The hydrolysis products, recognized as indicative of fat consumption, trigger release of biochemical factors as part of feedback loops. For example, the hormone, cholecystokinin, is released which triggers a physiological response—closing of the pyloric sphincter—as well as a brain response to reduce the impulse to eat. When the pyloric sphincter is closed, the stomach is more likely to feel full, especially if there is additional food or beverage intake. There are many other biochemical factors involved in food intake control loops and the compositions of this invention may interact with some or all of these.

Lipophilic active agents may be formulated with triglycerides that yield shorter chain and/or saturated fatty acids and monoacylglycerols on hydrolysis. These triglyceride hydrolysis products are often taken up by an alternative mechanism not involving liposomal and micellar molecular aggregates but diffusion of individual molecules. As such, entry into the bloodstream that occurs via the portal vein with subsequent direct transit to the liver. In other words, the higher aqueous solubility of these hydrolysis products means that they do not need to remain associated with the supramolecular aggregates in order to remain dispersed. That is, the triglyceride hydrolysis products can diffuse as individual molecules to the enterocyte surface and then are processed differently (i.e. not processed via the chylomicron reassembly/repackaging) ending up in the portal vein which feeds directly to the liver. Co-formulation of lipophilic active agents with shorter chain and/or saturated lipids provides an alternative way to enhance their bioavailability, particularly for those with higher aqueous solubility. The particular combinations of triglycerides, lecithin and active agents that are effective can be readily determined by one having ordinary skill in the art. Entrapment of water soluble agents in the aqueous compartment of the HLCVs, produced from the shorter chain/saturated lipids, provides a method of delivering these agents—protected from the rigors of the stomach and in highly dispersed form—to the duodenum for facile release, with resulting improved bioavailability compared to an active agent that is not entrapped in an HLCV. According to embodiments of the present invention, water soluble agents include known appetite suppressants. Non-limiting examples of known water soluble appetite suppressants include soluble fibers and phytochemicals.

The following Examples are presented for illustrative purposes only, and do not limit the scope or content of the present application.

EXAMPLES

Example 1

Flavored Triglyceride-Lecithin Composition

A composition of 300 mL corn oil, 300 mL olive oil and 800 g of lecithin with 75 mL 95% (v/v) ethanol and 2.5 mL lemon oil was prepared in 6 liters (L) conditioned water according to the method outlined in U.S. patent application Ser. No. 13/135,057, with homogenization at approximately 60° C. and a pressure of approximately 650 bar. Of the resulting 8 L of dispersion of triglycerides, a 4 L aliquot was mixed with 2 L of an acidulant solution containing 105 g/L citric acid, 87.5 g/L sodium citrate, 175 g/L sucrose, 1.75 g/L sodium benzoate and 35 g/L partially hydrolyzed guar gum. To this mixture was added 11.5 L purified water, 10 mL lemon extract, 4 mL strawberry flavoring, and 7 mL 25% (w/v) sucralose solution. Final pH was less than 4.5. The volume weighted mean diameter of the dispersion, as measured by the controlled reference method of dynamic light scattering, was about 0.15 micron. Consumption of 250 ml of the final dilution of the triglyceride composition induced a feeling of stomach fullness and reduced appetite. A control preparation, comprising the same amount of triglyceride per 250 ml shaken in sugar water, without lecithin, did not induce the same effects.

Example 2

Satiety and Weight Loss Study with Triqlyceride Composition

A cohort of 12 volunteers, 7 male and 5 female, having an age range of 14 to 72 years, initial weight 61 kg to 130 kg, Body Mass Index (a measure of body fat) 23.0 to 34.9, and body surface area from 1.73 to 2.39 square meters, were assigned to one or two daily servings of triglyceride formulation prepared as outlined in Example 1. Participants were instructed to consume a serving of the formulation approximately 60 minutes before dinner (and for the two daily serving group also about one hour before lunch). Participants recorded their morning weight daily and their perceived hunger before each suppressant serving and immediately before the corresponding meal. Using a standard Visual Analog Scale—a 100 mm long horizontal straight line with extremes designated "not at all hungry" (left) and "extremely hungry" (right)—hunger level was recorded by making a mark crossing the scale. Measuring the position of the mark relative to the left hand end ("not at all hungry") was used to quantitate appetite. While inter-participant perception of hunger on the scale was unknown, the change in the appetite value for a given participant was presumed indicative of appetite change. Results for consumption of the formulation for 14 days are shown in FIG. 1 (average weight change as a percent of starting weight) and Table 1.

TABLE 1

| weight change vs day 1 | # observations | | wt. change | | | |
|---|---|---|---|---|---|---|
| | possible | recorded | gain | zero | loss | "controlled*" |
| All participants (n = 12) | 156 | 131 | 15 | 9 | 107 | 116  89% |
| *= unchanged or weight loss | | | | | | |

| HUNGER VAS Scale | Change in hunger: pre-supplement to before meal | | | | | |
|---|---|---|---|---|---|---|
| (as mm reduction) | Lunch | | Dinner | | All meals | |
| All participants (n = 12) | mean | std. dev. | mean | std. dev. | mean | std. dev. |
| 1 serving daily | | | 7.3 | 3.0 | 6.4 | 4.9 |
| 2 servings daily all participants | 7.0 | 5.8 | 4.9 | 5.4 | | |

Example 3

Alcohol Uptake Inhibition

Figure 2:
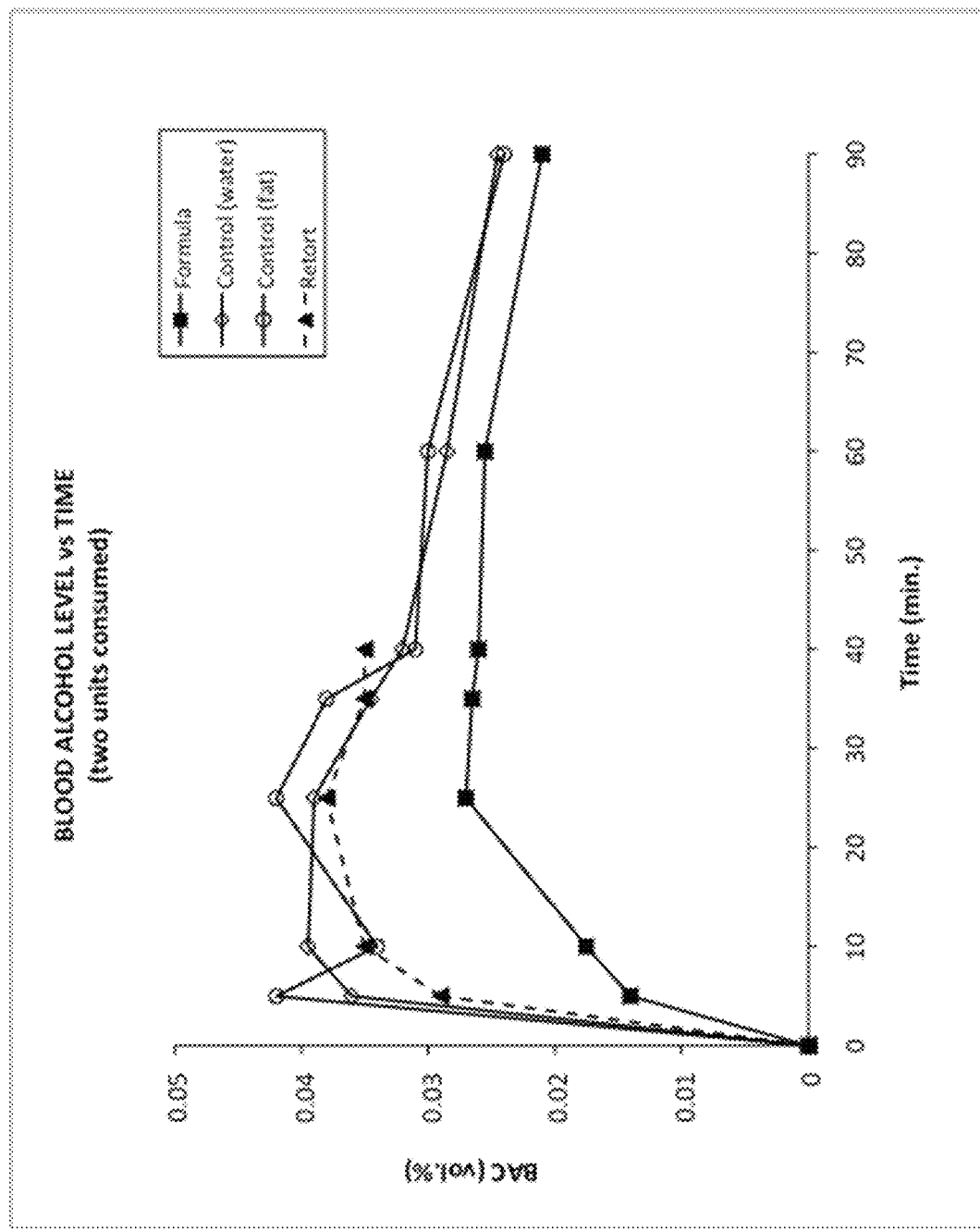
FIG. 2 is a graph comparing the percent blood alcohol content (BAC) over time (minutes) of an adult male comparing the BAC levels after consumption of alcohol and after consumption of a Formula composition (closed squares), a water Control composition (open diamonds), a fat Control composition (open circles), or a Retort composition (closed triangles), as described in Example 3, according to some embodiments of the present invention.

It is well established that consumption of fat results in activation of a feedback loop of which one component is closing the pyloric sphincter, the valve at the lower end of the stomach. If this valve is closed when an alcoholic beverage, such as beer, is consumed, uptake of alcohol into the bloodstream is inhibited. In contrast, alcohol drunk on an empty stomach is rapidly absorbed and "goes straight to the head." These effects occur because alcohol uptake in the duodenum, (immediately below the pyloric sphincter) occurs quickly, whereas the diffusion of alcohol from the stomach into the bloodstream is slow. In most cases, 20% of the alcohol in a drink is absorbed through the stomach and 80% through the small intestine. For compositions according to embodiments of the present invention, the relative effects on the fat intake feedback loop may therefore be assessed using blood alcohol content (BAC) measurements, which may be obtained using a breathalyzer device. The results of this study are shown in FIG. 2. BAC with and without prior consumption of a particular composition indicates the relative extent to which the feedback loop has been activated.

Using a hand-held Blood Alcohol Content (BAC) meter, exhaled breath analysis was used to determine BAC for an adult male. Levels were determined before consuming alcoholic beverages and at intervals up to 90 minutes after. In the "water" control, breath analysis was taken 15 minutes after consumption of 250 ml of water over a period of less than two minutes. Then either one or two units of alcohol (one unit is a 12 oz./300 ml beer with 4.5 vol. % alcohol) was consumed over a 15-minute interval, the end of which was set as t=0. BAC measurements were taken following rinsing of the mouth with water and a five minute delay in order to minimize interference from any residual alcohol in the oral cavity. For test experiments, the test article ("Formula") was consumed over a period of less than two minutes commencing 15 minutes before the start of alcoholic beverage consumption. FIG. 2 shows results for consumption of two units of alcohol. The control data represent the mean of two determinations. The FORMULA was 250 ml of a triglyceride formulation prepared by the method described in Example 1 and containing 1.25 g corn oil, 1.25 g canola oil and 3.75 g lecithin in HLCVs—data are the mean of duplicate studies. A further "fat" control was measured. This "fat" control included a shaken mixture of the same components as in the test FORMULA but without lecithin, and was consumed prior to the alcoholic beverage. In this lipid ("fat") control, the amount of triglyceride was increased to compensate for the fat content of the missing lecithin. In this case, alcohol uptake was not moderated by the "fat" control. In addition to the reduction in the BAC peak and area under the curve, the triglyceride-lecithin compositions induced a feeling of stomach fullness that caused significant discomfort as the second 12 oz. beer was consumed (a discomfort not sensed if triglyceride was not consumed). FIG. 2 also illustrates a "Retort" control to measure the effect of autoclaving a formulation of this invention on its ability to modify alcohol uptake. The BAC profile for autoclaved material closely resembles that for the control tests. This result is presumed to indicate that the alteration of the chemical and physical structure of the hydrated lecithin carrier vesicles, induced by the extreme conditions of autoclaving, alters their physiological processing after ingestion.

Example 4

Alternative Formula for Inhibiting Alcohol Uptake

Figure 3:
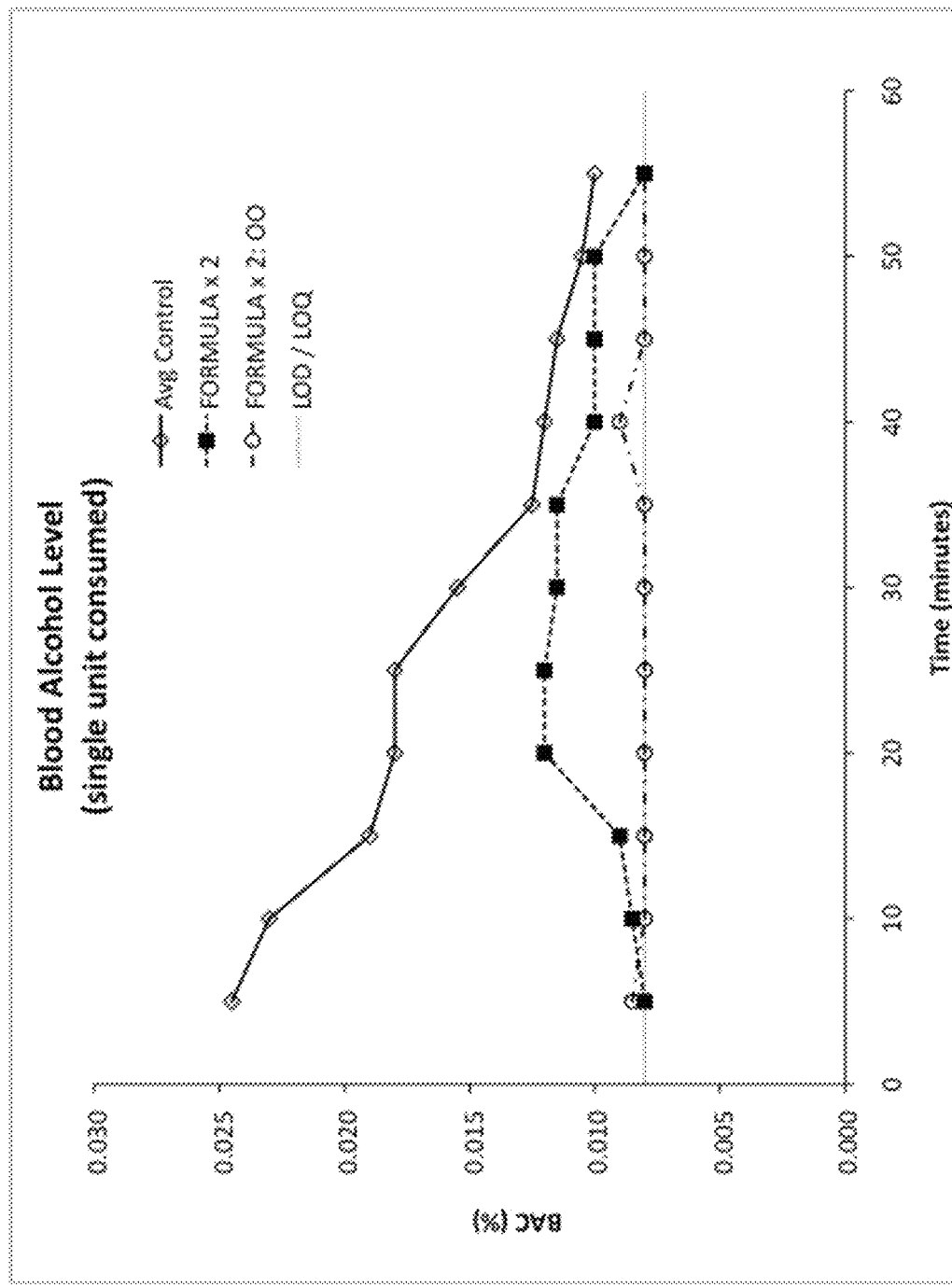
FIG. 3 is a graph comparing the percent BAC over time (minutes) an adult male, after consumption of alcohol and after consumption of a composition of a water control (open diamonds), Formula x 2 (closed squares), or a Formula x2:OO (open circles), as described in Example 4, according to some embodiments of the present invention.

FIG. 3 shows the results of a similar study in which a single unit of alcohol was consumed. The test formula (FORMULA x 2; dotted line through dark squares) was prepared as described in Example 3, but at twice the amount of the lecithin triglyceride mixture. An alternative test formula was prepared using olive oil in place of canola oil, also at twice the amount of lipids (FORMULA x 2: OO; detached line through open circles). The Avg Control is the Water control as performed in Example 3. The LOD/LOQ shows the level of detection (LOD) over the level of quantification (LOQ) for this BAC assay. Relative to the two units of alcohol example, less stomach discomfort was experienced, but fullness was sensed with the triglyceride preparations. Results shown in FIG. 3 (the average of duplicate experiments) demonstrate the reduction of blood alcohol levels with the test formulas. For the olive oil formulation, an improved effect is found with the rate of uptake essentially slowed to match the rate of metabolism of the alcohol in the bloodstream: the BAC remains at or close to the limit of detection of the BAC assay. The breathalyzer instrument used registers zero for any BAC at or below 0.008%—conservatively, the figures show such "zero" results as 0.008%, the limit of detection/quantitation, although the true BAC may actually be lower. Various combinations of triglycerides (and components) with lecithin were tested for their ability to modulate BAC: results are summarized in Table 2 below. The effect of buffer is considered in Example 4, but a pairwise comparison shows that peak BAC levels are delayed and or/reduced more, relative to the control, for formulations with a greater degree of mono- and tri-unsaturation (averaged over all triglyceride components).

TABLE 2

| COMPOSITION | QTY. | VOL. | PEAK BAC | PEAK TIME |
|---|---|---|---|---|
| control (water) | — | 250 ml | 0.025% | 5 min |
| corn oil:palmitic acid (100:2.5) | 5 g | 200 ml | 0.018% | 20 min |
| corn oil:canola oil:palmitic acid (50:50:2.5) | 5 g | 200 ml | 0.018% | 25 min |
| corn oil:canola oil (50:50) buffered | 5 g | 250 ml | 0.012% | 20 min |
| corn oil:olive oil (50:50) buffered | 5 g | 250 ml | 0.009% | 40 min |

Example 5

Bent Chain Acyl Groups for Enhanced Fat Intake Signaling

Figure 4B:
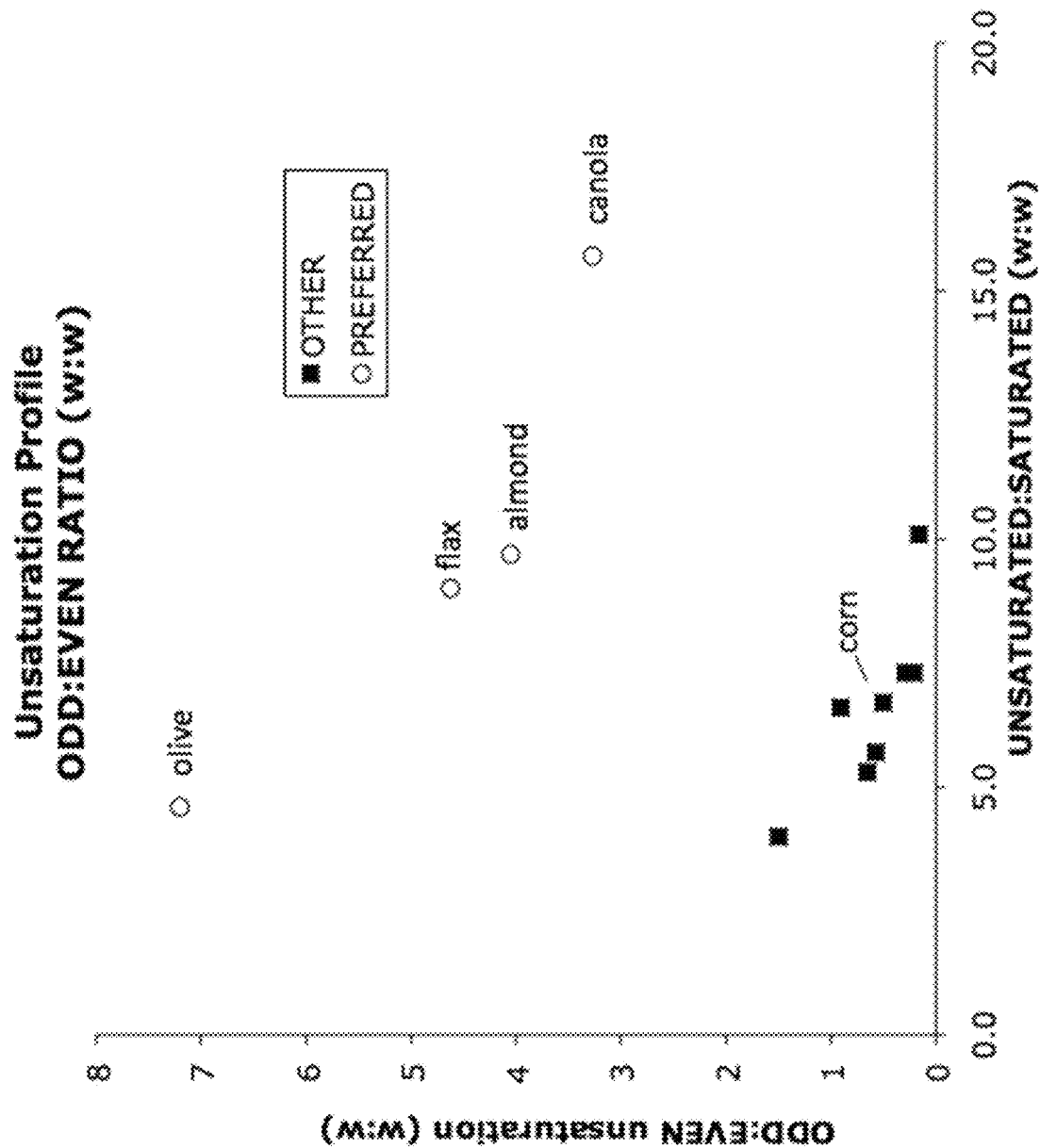
FIG. 4B is an unsaturation profile showing the weight ratio (w:w) of unsaturation from mono- and tri-unsaturated fatty acids (ODD) to that from di-unsaturated acids (EVEN) as a function of the weight ratio (w:w) of the overall unsaturated to saturated fatty acids, as described in Example 5, for triglyceride sources in some embodiments of the present invention.

Without being bound by a particular theory for the mechanism of action, it is proposed that the presence of "bent chain" acyl groups, such as oleic and alpha-linolenic acids, either engender sufficient disorder in the lipid bilayer structures of embodiments of the invention for enzymatic hydrolysis to be especially well facilitated and/or provide for enhanced fat intake signaling upon uptake by enterocytes. Canola oil and olive oil are examples of suitable triglycerides as are flaxseed and almond oils, based on their compositions. These oils have unsaturation profiles, illustrated in FIGS. 4A and 4B, that set them apart from other common dietary fats. "OTHER" in these figures refers to: corn, peanut, sesame, walnut, soybean, sunflower, grape and safflower oils. In FIG. 4B the odd:even ratio is the ratio of unsaturation from mono- and tri-unsaturated fatty acids to that from di-unsaturated acids. It should be noted that unless they are conjugated, di-unsaturated fatty acids do not provide the same membrane disordering potential as mono- and tri-unsaturated acyl groups. Although it produces a modulation of BAC, corn oil that is rich in C18:2 linoleic acid less effective at BAC peak reduction than a mixture of corn oil with olive oil. (C18:2 linoleic acid that has an 18-carbon chain and two cis double bonds.) Exemplary triglyceride mixtures in some embodiments of this invention are high in unsaturation and/or have a high proportion of mono- and tri-unsaturated acids in their unsaturated fatty acids. It is noted that fish and algal oils are not common dietary fats, and their high content of the highly polyunsaturated fatty acids EPA and DHA (with 5 and 6 double bonds, respectively) produce significant bilayer disorder in phospholipid bilayers in which they are incorporated.

Example 6 pH of Lecithin Composition

Figure 5:
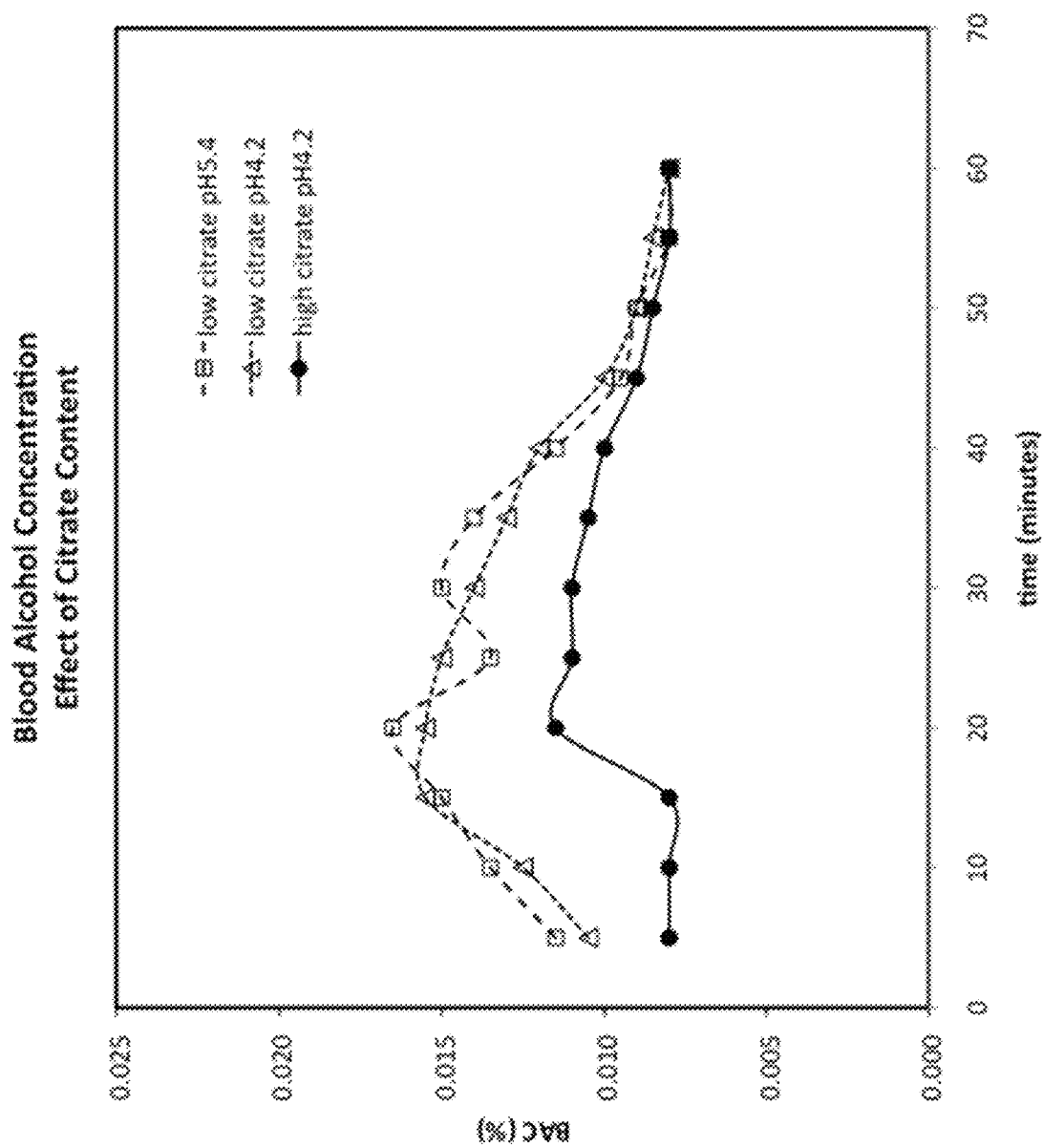
FIG. 5 is a graph of the BAC over time for compositions having "low citrate pH 5.4" (open squares), "low citrate pH 4.2" (open triangles), or "high citrate pH 4.2" (closed circles), as described in Example 6, according to embodiments of the present invention.

In order to maintain a dispersed state on exposure to stomach acid, the compositions according to embodiments of the invention should preferably remain at a pH above the pK of the charged phospholipids of their constituent lecithin (e.g., pK of 2.5-3.0). The amount and acidity of gastric fluid present in the human stomach varies widely. However, use of a suitable physiologically acceptable food acidulant (such as those added for flavor profile and pH adjustment) can provide sufficient buffer capacity to maintain stomach pH in an acceptable range. There are several known suitable acidulants, and concentrations and starting pHs thereof, that can provide this buffer capacity. FIG. 5 shows the BAC profiles for a formulation prepared as described in Example 4 with 2.5 g mixed triglycerides and 3.75 g soy lecithin in each 250 ml. The upper curves are for a samples containing 2 g citric acid at pH 5.4 or 4.2. The pH 5.4 data are the average of results from samples with triglyceride compositions of 1:1 corn oil:canola oil and 1:1 corn oil:olive oil. All other data are averages of duplicate 1:1 corn oil:olive oil triglyceride mixture sample results and shows reduced BAC levels below the control study levels of FIG. 3, but not as low as the test formulation data. With all other component proportions maintained constant, the lower curve demonstrates the effect of doubling the citric acid content (to 4 g) to a level where exposure of the HLCVs to unacceptably low pH is avoided, and a greater reduction in BAC is observed.

Example 7

Reduced Alcohol Flushing Syndrome

Figure 7A:
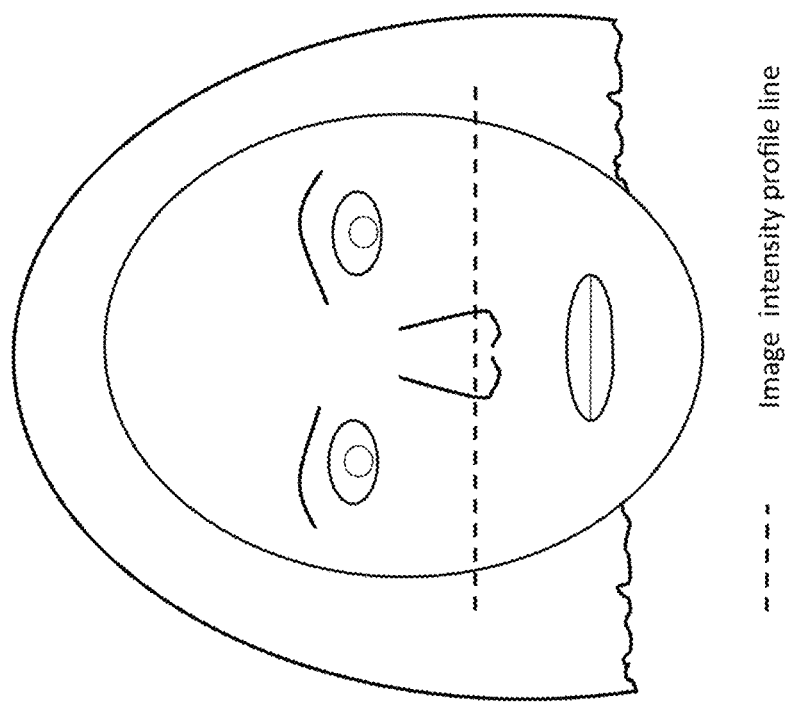
FIG. 7A is a schematic of a face showing an image intensity line indicating the image area that was analyzed using image software to analyze flushing of the face, as described in Example 7, according to embodiments of the present invention.

Inhibition of alcohol uptake may also be monitored, in susceptible individuals, by observations of alcohol flushing syndrome. Those with a particular gene variant, most often of Asian descent, have low levels of the aldehyde dehydrogenase enzyme. Thus, alcohol that enters their bloodstream is metabolized to acetaldehyde which is not efficiently degraded, and consequently builds up to toxic levels. The toxicity most obviously manifests as skin flushing and accelerated heart rate. An adult Asian female with known alcohol flushing syndrome was monitored for heart rate, using a fingertip pulse oximeter (Facelake CMS50D+) with data subsequently downloaded by USB cable to a computer for display and print out, and for facial appearance using digital photography with image analysis. In a control study, one half glass (75 ml) of white wine (13 vol. % alcohol) was consumed in three 25 ml aliquots at fifteen minute intervals after which monitoring was continued for one hour. Both tachycardia (elevated heart rate) and deep red facial flushing were apparent within 30 minutes of consuming the first aliquot of alcohol. In the test study, the procedure was repeated approximately 20 minutes after consuming the triglyceride formulation of Example 3. FIG. 6 shows the heart rate traces from the control and test procedures. The alcohol-induced elevation of heart rate is clearly seen for this susceptible individual but this tachycardia is effectively eliminated in the test case when the triglyceride formulation is consumed before the wine. In addition, photographs were taken full-face without flash and stored as JPEG images that were rendered in grayscale and analyzed for intensity using Image-J, a public domain Java image-processing program based on United States National Institutes of Health image analysis software. The image intensity profile was obtained left to right along a horizontal line starting and finishing in the subject's hair and crossing the tip of the nose (lines shown in FIG. 7A). The hair provides a low intensity region at each extreme of the profile and the tip of the subject's nose (very reflective in the images) is a high intensity marker. To adjust for variations in distance from the camera and positioning in the field of view, profile horizontal scales were normalized to the same width by linear scaling and images were registered (i.e. left or right shifted) to align the shadows at the edge of the nostrils on either side of the nose. Shown in FIG. 7B, the essentially overlapping upper traces correspond to images from before the consumption of alcohol (CONTROL) and after consumption when the formulation of the invention was consumed beforehand (FORMULA). In the alcohol consumption case, facial flushing in which the skin color changes from a light flesh tone to a dark red appearance is clearly seen as a significant decrease in intensity in the two portions of the profile corresponding to the cheeks (ALCOHOL).

Example 8

Pharmacokinetics (PK)-Bioavailability

Figure 8:
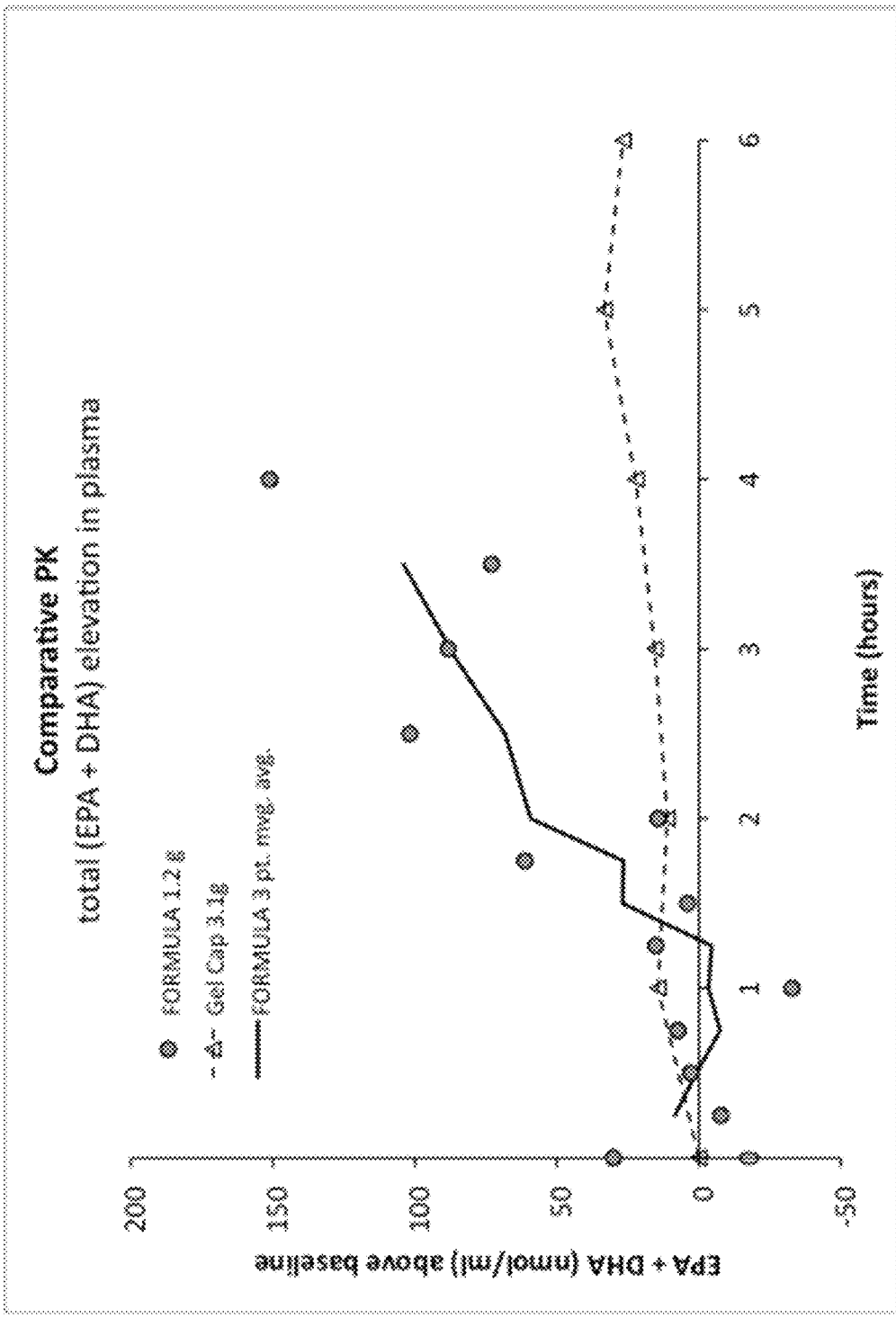
FIG. 8 is a graph showing the total elevation of eicosapentaenoic acid (EPA) and docosahexaenoic acid (DHA) in plasma over time after consumption of the disclosed Formula having 1.2 g of EPA/DHA (closed circles; the 3 point moving average shown as a solid line), and a comparative omega-3 gel cap (open triangles) as described Example 8, according to embodiments of the present invention.

Following an overnight fast, a male volunteer consumed 1.2 g of EPA+DHA formulated as 4 g 18:12 fish oil triglycerides (18% EPA and 12% DHA) with 6 g lecithin and prepared as described in Example 1. Elevation of plasma levels of the EPA and DHA omega-3 fatty acids was subsequently monitored at 15-30 minute intervals. The fatty acids were analyzed by gas chromatography-mass spectrometry (GCMS) following plasma extraction, triglyceride acid hydrolysis, derivatization with pentafluorobenzyl bromide (PFBBr) and further extraction, An internal free fatty acid standard was used in the assays. Blood plasma levels are shown in FIG. 8, with the three-point moving average shown as a solid line. For comparison, FIG. 8 also illustrates the data for a prescription omega-3 gel cap product (4 g total triglyceride dose, 3.1 g DHA+EPA; Lovaza) taken with a low fat diet. Even at a 2.5 times lower dose, the triglyceride-lecithin formulation produces a notably greater omega-3 plasma level enhancement than the gel cap. (The control omega-3 gel cap was disclosed in Davidson et al., Poster Presentation DALM XVII International Symposium, Doha, Qater, March 2011.)

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A composition, comprising a stable homogeneous dispersion, comprising:
   a liposomal vesicle composition having a lecithin bilayer and an aqueous phase, the liposomal vesicle composition, comprising:
      a lecithin from oil-bearing seeds having phosphatidylethanolamine (PE), phosphatidylinositol (PI), and 20 to 70 w/w % phosphatidylcholine (PC);
      a lipophilic active ingredient incorporated within the lecithin bilayer of the liposomal vesicle;
      a triglyceride source incorporated within the lecithin bilayer of the liposomal vesicle; and
      conditioned water, the conditioned water having less than 100 parts per million (ppm) hard ions or having a conductivity of less than 20 microSiemens per centimeter.

2. The composition of claim 1, wherein the liposomal vesicle has a volume-weighted mean diameter of about 500 nm or less.

3. The composition of claim 1, wherein the triglyceride source has an overall unsaturated fatty acid to saturated fatty acid ratio of at least 4:1 by weight.

4. The composition of claim 1, wherein the triglyceride source has a ratio of the sum of mono-unsaturated fatty acids and tri-unsaturated fatty acids to di-unsaturated fatty acids of at least 1:1.

5. The composition of claim 1, wherein the triglyceride source has an average oleic acid content of at least 40% by weight based on the total weight of fatty acids in the triglyceride source.

6. The composition of claim 1, wherein the triglyceride source comprises olive oil, canola oil, almond oil, flaxseed oil, or combinations thereof.

7. The composition of claim 6, wherein the triglyceride source is at most 50% by weight based on the total weight of the lecithin and the triglyceride source.

8. The composition of claim 7, wherein the triglyceride source is a mixture of corn oil and olive oil.

9. The composition of claim 1, further comprising an acidulant buffer.

10. The composition of claim 9, wherein the acidulant buffer is present in a molar ratio of acidulant buffer to lecithin of about 0.1:1 to about 5:1.

11. The composition of claim 9, wherein the molar ratio of acidulant buffer to lecithin is at least 5:1.

12. The composition of claim 1, further comprising a water soluble agent.

13. The composition of claim 1 wherein the triglyceride source comprises carbon chain lengths of less than 14 carbons and/or saturated fatty acids.

14. The composition of claim 12, wherein the water soluble agent is an appetite suppressant.

15. The composition of claim 14, wherein the appetite suppressant is a soluble fiber, a phytochemical, or a combination thereof.

16. The composition of claim 1, wherein the lecithin from oil-bearing seeds is a Generally Regarded As Safe (GRAS) lecithin from an oil selected from the group consisting of soy oils.

17. The composition of claim 1, wherein the lecithin from oil-bearing seeds having 20 to 70 w/w % PC has 20 to 60 w/w % PC.

18. A composition, comprising a stable homogenous dispersion, comprising:
    A liposomal vesicle composition having a lecithin bilayer and an aqueous phase, the liposomal vesicle composition, comprising:
        a lecithin from an oil selected from the group consisting of soy oils the lecithin being a Generally Regarded As Safe (GRAS) lecithin having phosphatidylethanolamine (PE), phosphatidylinositol (PI), and 20 to 70 w/w % phosphatidylcholine (PC);
        a lipophilic active ingredient incorporated within the lecithin bilayer of the liposomal vesicle;
        a triglyceride source incorporated within the lecithin bilayer of the liposomal vesicle; and
        conditioned water, the conditioned water having less than 100 parts per million (ppm) hard ions or having a conductivity of less than 20 microSiemens per centimeter.

19. The composition of claim 18, wherein the triglyceride source comprises an omega-3 fatty acid or a mixture of omega-3 fatty acids.

20. The composition of claim 18, wherein the triglyceride source comprises eicosapentaenoic acid (EPA) and/or docosahexaenoic acid (DHA).

21. The composition of claim 18, wherein the lecithin having 20 to 70 w/w % PC has 20 to 60 w/w % PC.

* * * * *